(12) United States Patent
Kubota et al.

(10) Patent No.: US 8,314,240 B2
(45) Date of Patent: Nov. 20, 2012

(54) SULFONAMIDE COMPOUNDS OR SALTS THEREOF

(75) Inventors: Hideki Kubota, Tokyo (JP); Issei Tsukamoto, Tokyo (JP); Kazunori Kamijo, Tokyo (JP); Koji Kato, Tokyo (JP); Yuta Fukuda, Tokyo (JP); Hidenori Azami, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 2 days.

(21) Appl. No.: 13/000,677

(22) PCT Filed: Jun. 22, 2009

(86) PCT No.: PCT/JP2009/061288
§ 371 (c)(1),
(2), (4) Date: Dec. 22, 2010

(87) PCT Pub. No.: WO2009/157399
PCT Pub. Date: Dec. 30, 2009

(65) Prior Publication Data
US 2011/0201616 A1      Aug. 18, 2011

(30) Foreign Application Priority Data
Jun. 23, 2008   (JP) .................................. 2008-163739

(51) Int. Cl.
*A61K 31/44* (2006.01)
*C07D 213/62* (2006.01)
(52) U.S. Cl. ......... 546/261; 546/294; 514/335; 514/347
(58) Field of Classification Search ........................ None
See application file for complete search history.

(56) References Cited

U.S. PATENT DOCUMENTS

| 2005/0020646 A1 | 1/2005 | Newgreen et al. |
| 2005/0124672 A1 | 6/2005 | Naganawa et al. |
| 2006/0100195 A1 | 5/2006 | Maruyama et al. |

FOREIGN PATENT DOCUMENTS

| JP | 2004 99493 | 4/2004 |
| JP | 2008 214224 | 9/2008 |
| WO | 98 27053 | 6/1998 |
| WO | 00 69465 | 11/2000 |
| WO | 02 072564 | 9/2002 |
| WO | 2004 099127 | 11/2004 |
| WO | 2006 121097 | 11/2006 |
| WO | 2007 072782 | 6/2007 |

OTHER PUBLICATIONS

Silverman, R. "The Organic Chemistry of Drug Design and Drug Action," 2004, Elsevier, pp. 29-32.*
CAPLUS 2006 1206504.*
Abrams, P. et al., "The Standardisation of Terminology of Lower Urinary Tract Function: Report From the Standardisation Sub-Committee of the International Continence Society", Neurourology and Urodynamics, vol. 21, pp. 167-178 (2002).
Schuebler, B., "Comparison of the Mode of Action of Prostaglandin $E_2$ ($PGE_2$) and Sulprostone, a $PGE_2$-Derivative, on the Lower Urinary Tract in Healthy Women", Urological Research, vol. 18, No. 5, pp. 349-352, (1990).
Ishizuka, O. et al., "Prostaglandin $E_2$-Induced Bladder Hyperactivity in Normal, Conscious Rats: Involvement of Tachykinins?", The Journal of Urology, vol. 153, No. 6, pp. 2034-2038, (Jun. 1995).
"Pamphlet of General Assembly Proceedings of the 89th Japanese Urological Association", MP-305, Journal of the Japanese Urological Association, vol. 92, No. 2, p. 304, (Feb. 2001).
Nakayama, Y. et al., "Role of Prostaglandin Receptor $EP_1$ in the Spinal Dorsal Horn in Carrageenan-Induced Inflammatory Pain", Anesthesiology, vol. 97, No. 5, pp. 1254-1262, (Nov. 2002).
Omote, K. et al., "The Effects of Intrathecal Administration of an Antagonist for Prostaglandin E Receptor Subtype $EP_1$ on Mechanical and Thermal Hyperalgesia in a Rat Model of Postoperative Pain", Anesthesia and Analgesia, vol. 95, No. 6, pp. 1708-1712, (2002).
Kawahara, H. et al., "A Prostaglandin $E_2$ Receptor Subtype $EP_1$ Receptor Antagonist (ONO-8711) Reduces Hyperalgesia, Allodynia, and C-fos Gene Expression in Rats With Chronic Nerve Constriction", Pain Medicine, Anesthesia and Analgesia, vol. 93, No. 4, pp. 1012-1017, (2001).
Sarkar, S. et al.., "The Prostaglanding E2 Receptor-1 (EP-1) Mediates Acid-induced Visceral Pain Hypersensitivity in Humans", Gastroenterology, vol. 124, No. 1, pp. 18-25, (Jan. 2003).
Naganawa, A. et al., "Discovery of New Chemical Leads for Selective EP1 Receptor Antagonists", Bioorganic & Medicinal Chemistry, vol. 14, pp. 5562-5577, (May 12, 2006).
Naganawa, A. et al., "Discovery of Heteroaryl Sulfonamides As New EP1 Receptor Selective Antagonists", Bioorganic & Medicinal Chemistry, vol. 14, pp. 6628-6639, (Jun. 19, 2006).
Naganawa, A. et al. "Further Optimization of Sulfonamide Analogs As EP1 Receptor Antagonists: Synthesis and Evaluation of Bioisosteres for the Carboxylic Acid Group", Bioorganic & Medicinal Chemistry, vol. 14, pp. 7121-7137, (Aug. 1, 2006).
Naganawa, A. et al. "Optimization of Sulfonamide Derivatives As Highly Selective EP1 Receptor Antagonists", Bioorganic & Medicinal Chemistry, vol. 14, pp. 7774-7789, (Aug. 22, 2006).
International Search Report issued Aug. 11, 2009 in PCT/JP09/061288 filed Jun. 22, 2009.

* cited by examiner

*Primary Examiner* — Janet Andres
*Assistant Examiner* — Heidi Reese
(74) *Attorney, Agent, or Firm* — Oblon, Spivak, McClelland, Maier & Neustadt, L.L.P.

(57) ABSTRACT

[Object] A compound which is useful as an EP1 receptor antagonist is provided.
[Means for Solution] The present inventors investigated EP1 receptor antagonists, and confirmed that a compound having a sulfonamide structure, in which the nitrogen atom of the sulfonamide structure is substituted with 2-fluoropropyl group, 3-fluoro-2-methylpropyl group or the like, has a potent EP1 receptor antagonistic action, thereby completing the present invention. The sulfonamide compound of the present invention has a potent EP1 receptor antagonistic action and can be used as an agent for preventing and/or treating a lower urinary tract symptom or the like.

15 Claims, No Drawings

SULFONAMIDE COMPOUNDS OR SALTS THEREOF

CROSS REFERENCES TO RELATED APPLICATIONS

This application is a 371 of International Patent Application No. PCT/JP2009/061288, filed on Jun. 22, 2009, and claims priority to Japanese Patent Application No. 2008-163739, filed on Jun. 23, 2008.

TECHNICAL FIELD

The present invention relates to a sulfonamide compound or a salt thereof, which is useful as an active ingredient of a pharmaceutical composition, in particular, a pharmaceutical composition for treating a lower urinary tract symptom.

BACKGROUND ART

Overactive bladder that is one of the diseases which cause a lower urinary tract symptom refers to a clinical condition of the disease characterized by urinary urgency regardless of the presence or absence of incontinence, which is usually accompanied by pollakiuria and nocturia (Neurourology and Urodynamics, 21, 167-178 (2002)). For a treatment thereof, currently an anticholinergic agent is mainly used, and constant treatment results are obtained. However, it has been reported that the use thereof is difficult with patients with benign prostatic hyperplasia or elderly patients since it is known to cause side-effects such as dry mouth, constipation and blurred vision, as well as carrying a risk of urinary retention. In addition, it is known that there exist patients showing no improvement with treatment with the anticholinergic agent. In view of the above-mentioned facts, there are great expectations for a drug with a new mechanism of action for the overactive bladder.

Prostaglandin $E_2$ ($PGE_2$) is a bioactive substance for which arachidonic acid is used as a precursor, and is known to participate in regulation of the functions of the body through four subtypes of G protein-coupled receptors, i.e., EP 1, EP2, EP3, and EP4.

It is known that intravesical instillation of $PGE_2$ results in strong urinary urgency and reduction in the bladder capacity in human (Urological Research, 18(5), 349-352 (1990)), and that intravesical instillation of $PGE_2$ results in reduction in the bladder capacity of a rat (The Journal of Urology, 153(6), 2034-2038 (1995)), and a possibility that $PGE_2$ affects the function of the lower urinary tract is suggested. In recent years, it has been reported that administration of an EP1 receptor antagonist to a model rat with a spinal cord injury is useful in improving the voiding function (Journal of The Japanese Urological Association, February 2001, Vol. 92, No. 2, p. 304), that the abnormal voiding function of a model mouse with urethral stricture is eliminated by the knock-out of an EP1 receptor, and that exacerbation of the abnormal voiding function is shown with intravesical instillation of $PGE_2$ (Patent Document 1). Consequently, it is believed that the EP1 receptor antagonist is useful as an agent for treating a lower urinary tract symptom.

Moreover, with respect to the EP1 receptor antagonist, from the mechanism of action thereof, side effects specific to an anticholinergic agent are expected to be avoided, and in addition, an effect on patients who show no improvement by treatment with the anticholinergic agent can also be expected. Furthermore, this agent can be expected to further improve potent subjective symptoms by acting on sensory nerves. Furthermore, this agent has been reported to exhibit an effect of improving the clinical condition without lowering the voiding efficiency of a rat with spinal cord injury (General Assembly Proceedings of the 89th Japanese Urological Association (Kobe, 2001), pamphlet, MP-305), and thus it can be expected to be administered safely to patients with benign prostatic hyperplasia or elderly patients.

Furthermore, it is also widely known that $PGE_2$ is produced locally as an accompaniment to inflammation or tissue disorders, and is known to participate in expression of pain or fever as well as to enhance the inflammatory reaction. In recent years, it has become known that an EP 1 receptor antagonist shows efficacy in model animals with various types of pain such as inflammatory pain (Anesthesiology, 97(5), 1254-1262 (2002)), postoperative pain (Anesthesia and Analgesia, 95(6), 1708-1712 (2002)), and neuropathic pain (Anesthesia and Analgesia, 93(4), 1012-1017 (2001)). In addition, there have been reports on the clinical effect of administration of an EP1 receptor antagonist on visceral pain caused by hydrochloric acid (Gastroenterology, 124(1), 18-25 (2003)). From the above-mentioned facts, it is believed that the EP1 receptor antagonist is also useful as an agent for treating various types of pain.

Moreover, it is known that the EP1 receptor antagonist has an inhibitory action on aberrant crypt foci of the colonic mucosa, and on intestinal polyp formation (Patent Document 2), and it is believed that the EP 1 receptor antagonist is also useful as an agent for treating colon cancer, bladder cancer, prostate cancer, and the like.

As a sulfonamide compound having an EP 1 receptor antagonistic action, for example, compounds represented by the formulae (A), (B), (C), and (D) have been reported (Patent Documents 3, 4, 5, and 6, respectively).

[Chem. 1]

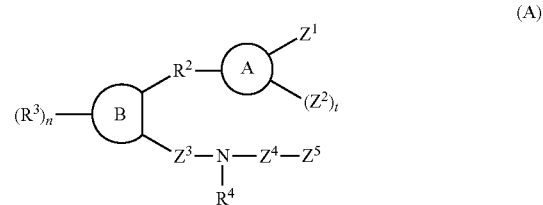

(A)

(In the formula above, $R^4$ represents (1) hydrogen, (2) C1 to 8 alkyl, C2 to 8 alkenyl, or C2 to 8 alkynyl, (3) C1 to 6 alkyl substituted with one or two groups selected from the group consisting of $COOZ^8$, $CONZ^9Z^{10}$, $OZ^8$ group, and C1 to 4 alkoxy-C1 to 4 alkoxy, (4) C3 to 7 cycloalkyl, or (5) C1 to 4 alkyl, C2 to 4 alkenyl, or C2 to 4 alkynyl, each substituted with phenyl or C3 to 7 cycloalkyl, and $Z^4$ represents $SO_2$ or CO. For the other symbols, reference can be made to the publication.)

[Chem. 2]

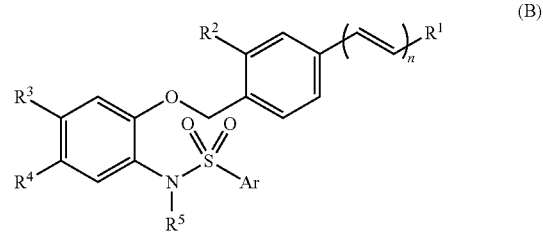

(B)

(In the formula above, $R^5$ represents isopropyl, isobutyl, 2-methyl-2-propenyl, cyclopropylmethyl, methyl, ethyl, propyl, 2-propenyl, or 2-hydroxy-2-methylpropyl. For the other symbols, reference can be made to the publication.)

[Chem. 3]

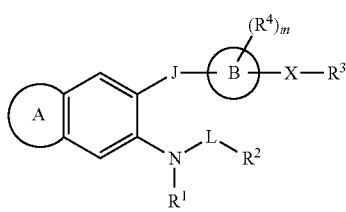

(C)

(In the formula above, Ring A represents 5- to 8-membered hetero ring which may be substituted. For the other symbols, reference can be made to the publication.)

[Chem. 4]

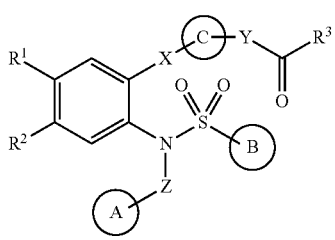

(D)

(In the formula above, A represents hetero ring group which may be substituted, and Z represents lower alkylene. For the other symbols, reference can be made to the publication.)

LIST OF THE DOCUMENTS

Patent Document

[Patent Document 1] Specification of US Patent Application Publication No. 2005/0020646
[Patent Document 2] Pamphlet of International Publication WO 00/069465
[Patent Document 3] Pamphlet of International Publication WO 98/027053
[Patent Document 4] Pamphlet of International Publication WO 02/072564
[Patent Document 5] Pamphlet of International Publication WO 06/121097
[Patent Document 6] Pamphlet of International Publication WO 07/072,782

SUMMARY OF THE INVENTION

Problem that the Invention is to Solve

A compound which is useful as an active ingredient of a pharmaceutical composition, in particular, a pharmaceutical composition for treating a lower urinary tract symptom is provided.

Means for Solving the Problem

The present inventors have conducted extensive studies on EP1 receptor antagonists, and as a result found that a compound of the formula (I) or a salt thereof has a potent EP1 receptor antagonistic action and improves the regarding pollakiuria condition excellently, thereby completing the present invention.

That is, the present invention relates to the compound of the formula (I) or a salt thereof, and a pharmaceutical composition containing the compound of the formula (I) or a salt thereof and an excipient.

[Chem. 5]

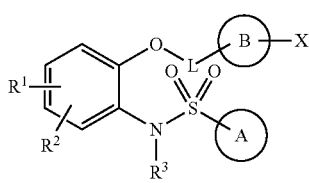

(I)

(wherein
$R^1$ and $R^2$ are the same as or different from each other, and represent H, halogen, $R^0$, halogeno-lower alkyl, —OH, or —O—$R^0$, or $R^1$ and $R^2$ may be combined with the two adjacent carbon atoms to which they each bind to form a 5- to 8-membered cycloalkene ring,
$R^3$ is 2-fluoropropyl, 2-fluorobutyl, 2,2-difluoroethyl, or 3-fluoro-2-methylpropyl,
L is lower alkylene,
A is phenyl which may be substituted or monocyclic heteroaryl which may be substituted,
B is phenylene which may be substituted or monocyclic heteroarylene which may be substituted,
X is —$CO_2R^0$, —$CO_2H$, or —CO—NH—$SO_2$—$R^0$, and
$R^0$ is lower alkyl.)
In this connection, unless otherwise specifically noted, a symbol in a chemical formula in the present specification is also used in another chemical formula, the same symbol has the same meaning.

Further, the present invention relates to a pharmaceutical composition for treating a lower urinary tract symptom containing the compound of the formula (I) or a salt thereof, that is, an agent for treating a lower urinary tract symptom containing the compound of the formula (I) or a salt thereof.

Further, the present invention relates to use of the compound of the formula (I) or a salt thereof for the manufacture of a pharmaceutical composition for treating a lower urinary tract symptom, and a method for treating a lower urinary tract symptom, comprising administering to a patient a effective amount of the compound of the formula (I) or a salt thereof.

Effect of the Invention

The compound of the formula (I) or a salt thereof has a potent EP1 receptor antagonistic action, and can be used as an agent for preventing and/or treating a lower urinary tract symptom or the like.

BEST MODE FOR CARRYING OUT THE INVENTION

Hereinbelow, the present invention is described in detail.
In the present specification, the "lower alkyl" is linear or branched alkyl having 1 to 6 carbon atoms (which is hereinafter simply referred to as $C_{1-6}$), for example, methyl, ethyl, n-propyl, isopropyl, n-butyl, isobutyl, sec-butyl, tert-butyl, n-pentyl, n-hexyl, or the like. In another embodiment, it is $C_{1-4}$ alkyl, and in still another embodiment, $C_{1-2}$ alkyl.

The "lower alkylene" is linear or branched $C_{1-6}$ alkylene, for example, methylene, ethylene, trimethylene, tetramethylene, pentamethylene, hexamethylene, propylene, methylmethylene, ethylethylene, 1,2-dimethylethylene, 1,1,2,2-tetramethylethylene, or the like. In another embodiment, it is $C_{1-4}$ alkylene, and in a further embodiment, $C_{1-2}$ alkylene.

The "halogen" means F, Cl, Br, or I.

The "halogeno-lower alkyl" refers to $C_{1-6}$ alkyl substituted with one or more halogens. In another embodiment, it is lower alkyl substituted with 1 to 5 halogens, in a further embodiment, $C_{1-2}$ alkyl substituted with 1 to 5 halogens, and in a further embodiment, trifluoromethyl.

The "5- to 8-membered cycloalkene ring" is a hydrocarbon ring having 5 to 8 carbon atoms, which has one double bond, and specifically, cyclopentene, cyclohexene, cycloheptene, or cyclooctene. In another embodiment, it is cycloheptene or cyclohexene, and in a further embodiment, cyclopentene.

The "$R^1$ and $R^2$ may be combined with the two adjacent carbon atoms to which they each bind to form a 5- to 8-membered cycloalkene ring" means that $R^1$ and $R^2$ may bind to the two adjacent carbon atoms on the benzene ring and form a 5- to 8-membered cycloalkene ring together with these carbon atoms. Specifically, it means that $R^1$ and $R^2$ may be combined with the benzene ring to which they bind, to represent indane, tetrahydronaphthalene, or the like. In another embodiment, $R^1$ and $R^2$ are combined with the benzene ring to which they bind, to represent indane.

The "monocyclic heteroaryl" is a monovalent group constituted with a monocyclic 5- or 6-membered aromatic ring containing 1 to 4 hetero atoms selected from oxygen, sulfur, and nitrogen, and a ring atom, sulfur or nitrogen, may be oxidized to form an oxide or a dioxide. It is, for example, pyridyl, pyrimidinyl, pyridazinyl, pyrazinyl, triazinyl, furyl, thienyl, pyrrolyl, oxazolyl, isoxazolyl, oxadiazolyl, thiazolyl, isothiazolyl, thiadiazolyl, imidazolyl, pyrazolyl, triazolyl, tetrazolyl, or the like. In another embodiment, it is furyl, thiazolyl, or pyridyl.

The "monocyclic heteroarylene" is a divalent group formed by the removal of any one hydrogen atom on the ring atoms of the above "monocyclic heteroaryl"; it is, for example, pyridinediyl, pyrimidinediyl, pyridazinediyl, pyrazinediyl, triazinediyl, furandiyl, thiophenediyl, pyrrolediyl, oxazolediyl, isoxazolediyl, oxadiazolediyl, thiazolediyl, isothiazolediyl, thiadiazolediyl, imidazolediyl, pyrazolediyl, triazolediyl, tetrazolediyl, or the like. In another embodiment, it is pyridinediyl, pyrimidinediyl, pyridazinediyl, pyrazinediyl, thiophenediyl, or thiazolediyl.

The "phenylene" is a divalent group formed by the removal of any hydrogen atom of phenyl, and specifically, it is 1,2-phenylene, 1,3-phenylene, or 1,4-phenylene. In another embodiment, it is 1,4-phenylene.

In the present specification, "which may be substituted" means unsubstituted or having 1 to 5 substituents, and in another embodiment, 1 to 3 substituents. Further, if it has a plurality of substituents, the substituents may be the same as or different from each other.

Examples of the substituent in the "phenyl which may be substituted" or "monocyclic heteroaryl which may be substituted" of A, and "phenylene which may be substituted" or "monocyclic heteroarylene which may be substituted" of B include groups selected from the group consisting of halogen, lower alkyl, halogeno-lower alkyl, —OH, and —O-lower alkyl, and in another embodiment, groups selected from the group consisting of halogen, lower alkyl, and —O-lower alkyl.

Some embodiments of the compound of the formula (I) are presented below.

(1) The compound in which $R^1$ and $R^2$ are the same as or different from each other, and are halogen, $R^0$, halogeno-lower alkyl, or —O—$R^0$, or $R^1$ and $R^2$ may be combined with the two adjacent carbon atoms to which they each bind, to form a cyclopentene ring or cyclohexene ring. In another embodiment, the compound in which $R^1$ and $R^2$ are the same as or different from each other, and are halogen or $R^0$, or $R^1$ and $R^2$ may be combined with the two adjacent carbon atoms to which they each bind, to form cyclopentene ring. In a further embodiment, the compound in which $R^1$ and $R^2$ are the same as or different from each other, and are halogen or $R^0$. In a further embodiment, the compound in which $R^1$ and $R^2$ may be combined with the two adjacent carbon atoms to which they each bind, to form cyclopentene ring.

(2) The compound in which $R^3$ is 2-fluoropropyl, 2-fluorobutyl, or 3-fluoro-2-methylpropyl. In another embodiment, the compound in which $R^3$ is 2-fluoropropyl. In another embodiment, the compound in which $R^3$ is 2-fluorobutyl. In a further embodiment, the compound in which $R^3$ is 3-fluoro-2-methylpropyl.

(3) The compound in which L is methylene.

(4) The compound in which A is phenyl substituted with halogen(s), furyl substituted with methyl(s), thiazolyl substituted with methyl(s), 2-pyridyl, or 3-pyridyl. In another embodiment, the compound in which A is thiazolyl substituted with methyl(s), 2-pyridyl, or 3-pyridyl. In another embodiment, the compound in which A is thiazolyl substituted with methyl(s). In a further embodiment, the compound in which A is 2-pyridyl or 3-pyridyl.

(5) The compound in which B is thiophenediyl, pyridinediyl, pyrimidinediyl, or phenylene which may be substituted with one group selected from the group consisting of methyl, F, and methoxy. In another embodiment, the compound in which B is thiophenediyl, or phenylene which may be substituted with one group selected from the group consisting of methyl, F, and methoxy. In a further embodiment, the compound in which B is phenylene.

(6) The compound in which X is, —$CO_2H$ or —CO—NH—$SO_2$—$R^0$. In another embodiment, the compound in which X is —$CO_2H$.

(7) The compound which is a combination of two or more of the groups as described (1) to (6).

Specifically, the following combinations may be exemplified.

(8) The compound of the formula (I) in which L is methylene.

(9) The compound of (8), in which A is phenyl substituted with halogen(s), furyl substituted with methyl(s), thiazolyl substituted with methyl(s), 2-pyridyl, or 3-pyridyl.

(10) The compound of (9), in which X is —$CO_2H$ or —CO—NH—$SO_2$—$R^0$.

(11) The compound of (10), in which $R^3$ is 2-fluoropropyl, 2-fluorobutyl, or 3-fluoro-2-methylpropyl.

(12) The compound of (11), in which B is thiophenediyl, pyridinediyl, pyrimidinediyl, or phenylene which may be substituted with one group selected from the group consisting of methyl, F, and methoxy.

Specific examples of the compound encompassed by the present invention include the compound as described in (13) below, or a salt thereof

(13) 4-[(2-{[(2S)-2-fluoropropyl](pyridin-2-ylsulfonyl) amino}-4,5-dimethylphenoxy)methyl]benzoic acid,
4-[(2-{[(2R)-2-fluoropropyl](pyridin-2-ylsulfonyl)amino}-4,5-dimethylphenoxy)methyl]benzoic acid, 4-{[(6-{[(2R)-2-fluoropropyl](pyridin-2-ylsulfonyl)
    amino}-2,3-dihydro-1H-inden-5-yl)oxy]methyl}benzoic
    acid,
4-[(5-chloro-2-{[(2S)-2-fluoropropyl] (pyridin-2-ylsulfonyl)
    amino}-4-methylphenoxy)methyl]benzoic acid,
4-[(5-chloro-2-{[(2R)-2-fluoropropyl](pyridin-2-ylsulfonyl)
    amino}-4-methylphenoxy)methyl]benzoic acid,
4-[(2-{[(2R)-3-fluoro-2-methylpropyl](pyridin-2-ylsulfo-
    nyl)amino}-4,5-dimethylphenoxy)methyl]benzoic acid,
4-[(2-{[(2S)-3-fluoro-2-methylpropyl](pyridin-2-ylsulfo-
    nyl)amino}-4,5-dimethylphenoxy)methyl]benzoic acid,
4-{[(6-{[(2R)-2-fluorobutyl](pyridin-2-ylsulfonyl)amino}-
    2,3-dihydro-1H-inden-5-yl)oxy]methyl}benzoic acid,
4-{[(6-{[(2S)-2-fluorobutyl](pyridin-2-ylsulfonyl)amino}-
    2,3-dihydro-1H-inden-5-yl)oxy]methyl}benzoic acid,
4-[(5-chloro-2-{[(2R)-2-fluoropropyl](pyridin-3-ylsulfonyl)
    amino}-4-methylphenoxy)methyl]benzoic acid,
4-[(5-chloro-2-{[(2S)-2-fluoropropyl](pyridin-3-ylsulfonyl)
    amino}-4-methylphenoxy)methyl]benzoic acid,
4-[(2-{[(2S)-2-fluoropropyl](pyridin-3-ylsulfonyl)amino}-
    4,5-dimethylphenoxy)methyl]benzoic acid,
4-[(2-{[(2R)-2-fluoropropyl](pyridin-3-ylsulfonyl)amino}-
    4,5-dimethylphenoxy)methyl]benzoic acid,
4-{[(6-{[(2S)-2-fluoropropyl](pyridin-3-ylsulfonyl)amino}-
    2,3-dihydro-1H-inden-5-yl)oxy]methyl}benzoic acid, and
4-{[(6-{[(2R)-2-fluoropropyl](pyridin-3-ylsulfonyl)
    amino}-2,3-dihydro-1H-inden-5-yl)oxy]methyl}benzoic
    acid.

The compound of the formula (I) may have tautomers or geometrical isomers in some cases, depending on the kind of substituents. In the present specification, the compound of the formula (I) shall be described in only one form of the isomer, yet the present invention includes other isomers, isolated forms of the isomers, or a mixture thereof.

In addition, the compound of the formula (I) may have asymmetric carbon atom(s) or axial asymmetry in some cases, and correspondingly, it may exist in the form of optical isomers. The present invention also includes an isolated form of these optical isomers of the compound of the formula (I) or a mixture thereof.

In addition, the pharmaceutically acceptable prodrugs of the compound represented by the formula (I) are also included in the present invention. The pharmaceutically acceptable prodrug refers to a compound having a group which can be converted into amino group, hydroxyl group, carboxyl group, or the like, by solvolysis or under a physiological condition. Examples of the group for forming a prodrug include those as described in Prog. Med., 5, 2157-2161 (1985) or "Iyakuhin no Kaihatsu (Pharmaceutical Research and Development)" (Hirokawa Publishing Company, 1990), vol. 7, Bunshi Sekkei (Drug Design), 163-198.

Furthermore, the salt of the compound of the formula (I) is a pharmaceutically acceptable salt of the compound of the formula (I) and may form an acid addition salt or a salt with a base, depending on the kind of substituents. Specifically, examples thereof include acid addition salts with inorganic acids such as hydrochloric acid, hydrobromic acid, hydroiodic acid, sulfuric acid, nitric acid, phosphoric acid, and the like, and salts with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or salts with organic bases such as methylamine, ethylamine, ethanolamine, lysine, ornithine, and the like, salts with various amino acids and amino acid derivatives such as acetylleucine and the like, ammonium salts, and others.

In addition, the present invention also includes various hydrates or solvates, and any of crystalline polymorphs of the compound of the formula (I) and a salt thereof. Also, the present invention includes compounds labeled with various radioactive or non-radioactive isotopes.

(Production Process)

The compound of the formula (I) and a salt thereof can be prepared by applying various known synthetic methods, using the characteristics based on their basic skeletons or the kind of substituents. At this time, depending on the type of the functional groups, it is in some cases effective, from the viewpoint of the preparation techniques, to substitute the functional group with an appropriate protective group (a group which is capable of being easily converted into the functional group), during the stage of starting material to intermediate. Examples of the protective group include the protective groups described in "Greene's Protective Groups in Organic Synthesis (4th edition, 2006)", written by P. G. M. Wuts and T. W. Greene, and the like, which may be appropriately selected and used depending on reaction conditions. In these methods, a desired compound can be obtained by introducing the protective group to carry out the reaction, and then, if desired, removing the protective group.

In addition, the prodrug of the compound of formula (I) can be prepared by introducing a specific group during the stage of starting material to intermediate, in the same manner as for the aforementioned protective groups, or by carrying out further reaction using the obtained compound of the formula (I). The reaction can be carried out by applying a method known to a person skilled in the art, such as common esterification, amidation, dehydration, and the like.

Hereinbelow, the representative production processes for the compound of the formula (I) will be described. Each of the production processes may also be carried out with reference to the References appended in the explanation. Further, the production processes of the present invention are not limited to the examples as shown below.

(Production Process 1)

[Chem. 6]

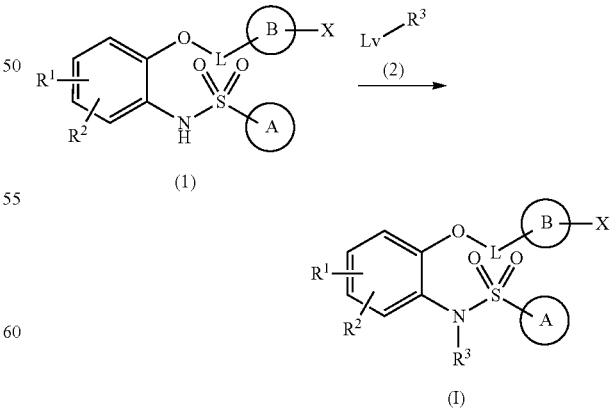

(In the formula, Lv represents a leaving group or —OH).

The compound (I) of the present invention can be obtained by the reaction of a compound (1) with a compound (2)

having a leaving group. Here, examples of the leaving group include halogen, methanesulfonyloxy, p-toluenesulfonyloxy group, and the like.

In this reaction, the compound (1) and the compound (2) having a leaving group are used in an equivalent amount or with either thereof in an excess amount, and the mixture thereof is stirred under from cooling to heating with reflux, preferably at 0° C. to 80° C., in a solvent which is inert to the reaction or without a solvent, usually for 0.1 hour to 5 days. The solvent used herein is not particularly limited, but examples thereof include aromatic hydrocarbons such as benzene, toluene, xylene, and the like, ethers such as diethyl ether, tetrahydrofuran (THF), dioxane, dimethoxyethane, and the like, halogenated hydrocarbons such as dichloromethane, 1,2-dichloroethane, chloroform, and the like, N,N-dimethylformamide (DMF), dimethylsulfoxide (DMSO), ethyl acetate, acetonitrile, and a mixture thereof. It may be advantageous in some cases for the smooth progress of the reaction to carry out the reaction in the presence of organic bases such as triethylamine, N,N-diisopropylethylamine, N-methylmorpholine, pyridine, 4-(N,N-dimethylamino)pyridine, potassium tert-butoxide, and the like, or inorganic bases such as potassium carbonate, cesium carbonate, sodium hydroxide, potassium hydroxide, sodium hydride, and the like.

REFERENCES

"Organic Functional Group Preparations", written by S. R. Sandler and W. Karo, 2nd Edition, Vol. 1, Academic Press Inc., 1991

"Jikken Kagaku Koza (Courses in Experimental Chemistry) (5th Edition)", edited by The Chemical Society of Japan, Vol. 14 (2005) (Maruzen)

Furthermore, the compound (I) of the present invention can also be obtained by Mitsunobu reaction of the compound (1) with the compound (2) in which Lv is —OH. This reaction can be carried out under from cooling to room temperature, preferably under from ice-cooling to at room temperature, in a solvent inert to the reaction, for example, ethers such as THF, dioxane, diethylether, and the like, halogenated hydrocarbons such as dichloromethane, chloroform, and the like, aromatic hydrocarbons such as toluene, benzene, and the like, DMF, or the like, in the presence of phosphine such as triphenylphosphine, tri-n-butylphosphine, tris(dimethylamino)phosphine, triphenylphosphite, diphenoxyphenylphosphine, diphenyl(2-pyridyl)phosphine, (4-dimethylamino)diphenylphosphine, and the like, and azodicarboxylate such as diethylazodicarboxylate, diisopropylazodicarboxylate, dimethylazodicarboxylate, and the like.

(Production Process 2)

[Chem. 7]

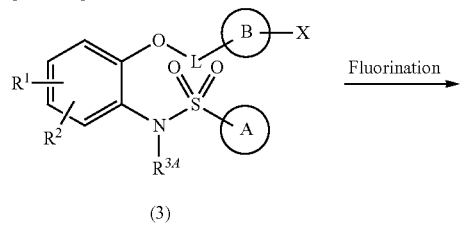

(3)

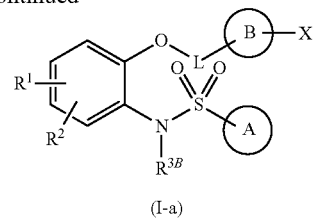

(I-a)

(In the formula, $R^{3A}$ represents 2-hydroxypropyl, 2-hydroxybutyl, or 3-hydroxy-2-methylpropyl, and $R^{3B}$ represents 2-fluoropropyl, 2-fluorobutyl, or 3-fluoro-2-methylpropyl)

In the formula (I), a compound (I-a) in which $R^3$ is 2-fluoropropyl, 2-fluorobutyl, or 3-fluoro-2-methylpropyl can also be obtained by fluorination of a hydroxyl group of a compound (3). This reaction can be carried out under from cooling to room temperature, preferably from −78° C. to under ice-cooling using a fluorination agent such as diethylaminosulfur trifluoride, morpholinosulfur trifluoride, 2,2-difluoro-1,3-dimethylimidazolidine, and the like, in a solvent inert to the reaction such as halogenated hydrocarbons, hexane, benzene, and the like.

REFERENCES

"Organic Reactions" written by M. Hudlicky, Vol. 35, Sections 513-633, John Wiley & Sons, 1988

"Jikken Kagaku Koza (Courses in Experimental Chemistry) (5th Edition)", edited by The Chemical Society of Japan, Vol. 13 (2005) (Maruzen)

(Production Process 3) Other Production Processes

Furthermore, several compounds represented by the formula (I) can also be prepared by subjecting the compound of the present invention obtained as above to any combination of the processes that can be usually employed by a person skilled in the art, such as hydrolysis, condensation, and the like. For example, these compounds can be prepared by the reactions as below, the methods described in Examples as described later, methods apparent to a person skilled in the art, or modified methods thereof.

3-1: Hydrolysis Reaction

The compound in which X is —CO$_2$H in the formula (I) can be obtained by the hydrolysis of the compound obtained by Production Process 1 in which X is —CO$_2$R$^0$. Here, the hydrolysis reaction can be carried out with reference to the above-mentioned "Greene's Protective Groups in Organic Synthesis (4th Edition, 2006)", edited by P. G. M. Wuts and T. W. Greene.

3-2: Condensation

The compound in which X is —CO—NH—SO$_2$—R$^0$ in the formula (I) can be obtained by the condensation of the compound in which X is —CO$_2$H with sulfonamide.

In this reaction, carboxylic acid and sulfonamide are used in an equivalent amount, or with either thereof in an excess amount, and the mixture thereof is stirred under from cooling to heating, preferably at from −20° C. to 60° C., usually for 0.1 hour to 5 days, in a solvent which is inert to the reaction, in the presence of a condensing agent. Examples of the solvent as used herein are not particularly limited, and include aromatic hydrocarbons such as benzene, toluene, xylene, and the like, halogenated hydrocarbons such as dichloromethane, 1,2-dichloroethane, chloroform, and the like, ethers such as diethylether, THF, dioxane, dimethoxyethane, and the like, DMF, DMSO, ethyl acetate, acetonitrile, and a mixture thereof. Examples of the condensing agent include 1-(3-dimethylaminopropyl)-3-ethylcarbodiimide, dicyclohexylcarbodiimide, 1,1'-carbonyldiimidazole, diphenylphosphoric azide, and phosphorus oxychloride, but are not limited thereto. It may be preferable for the reaction in some cases to use an additive (for example, 4-dimethylaminopyridine, 4-pyrrolidinopyridine, and the like). It may be advantageous in some cases for the smooth progress of the reaction to carry out the reaction in the presence of an organic base such as triethylamine, N,N-diisopropylethylamine, N-methylmorpholine, 1,8-diazabicyclo[5,4,0]undec-7-ene, and the like, or an inorganic base such as potassium carbonate, sodium carbonate, potassium hydroxide, sodium hydride, and the like.

Further, a method in which the carboxylic acid is converted into a reactive derivative thereof, and then the reactive derivative is reacted with sulfonamide can also be used. Here, examples of the reactive derivative of the carboxylic acid include acid halides that can be obtained by the reaction with a halogenating agent such as phosphorus oxychloride, thionyl chloride, and the like, mixed acid anhydrides that can be obtained by the reaction with isobutyl chloroformate or the like. The reaction of the reactive derivative and sulfonamide can be carried out under from cooling to heating, preferably at −20° C. to 60° C., in a solvent which is inert to the reaction, such as halogenated hydrocarbons, aromatic hydrocarbons, ethers, and the like.

(Starting Material Synthesis)

The starting compounds used in the Production Processes as described above can be prepared by employing, for example, the methods described in Patent Documents 3, 4, and 6 as mentioned above, the methods described in Preparative Examples as described below, methods apparent to a person skilled in the art, or modified methods thereof.

The compounds of formula (I) can be isolated and purified as their free compounds, salts, hydrates, solvates, or crystalline polymorphous substances thereof. The salts of the compounds of formula (I) can be prepared by subjecting to a conventional salt formation reaction.

Isolation and purification can be carried out by employing general chemical operations such as extraction, fractional crystallization, various types of fractional chromatography, and the like.

Various isomers can be prepared by selecting an appropriate starting compound or separated by making use of the difference in the physicochemical properties among the isomers. For example, the optical isomers can be obtained by means of general optical resolution methods of racemic products (for example, by fractional crystallization converting the compound into diastereomer salts with optically active bases or acids, by chromatography using a chiral column or the like, and others), or can also be prepared from an appropriate optically active starting compound.

The pharmacological activity of the compound of the formula (I) was confirmed by the following tests.

Test Example 1 Test to Measure Receptor Antagonistic Activity Using EP1 Receptor-Expressing Cells HEK293 cells (American Type Culture Collection) that stably expressed rat EP1 receptor were dispensed onto a 96-well poly-D-lysine-coated plate (product name: BIO-COAT, PDL96W black/clear, by Nippon Becton Dickinson) at $2\times10^4$ cells/well on the day before the experiment, and incubated overnight at 37° C. under 5% carbon dioxide ($CO_2$) in a culture medium containing 10% fetal bovine serum (FBS) (product name: DMEM, Invitrogen). The culture medium was replaced with a loading buffer (a washing solution containing 4 μM of fluorescent-labeled indicator (product name: Fluo3-AM, Dojindo): Hank's balanced salt solution (HBSS), 20 mM 2-[4-(2-hydroxyethyl)-1-piperazinyl] ethanesulfonic acid (HEPES)-sodium hydroxide (NaOH), 2.5 mM Probenecid, and 0.1% bovine serum albumin (BSA)), and left to stand at room temperature for 3 hours, and the cells were washed using a plate washer (product name: ELx405, Bio-Tek Instruments, Inc.) in which the washing solution had been set up. The compound that had been preliminarily dissolved and diluted in the washing solution was added thereto, and set up in a system for measuring the intracellular calcium (Ca) concentration (product name: FLIPR, Molecular Devices, Inc.). After 5 minutes, $PGE_2$ was added to a final concentration of 100 nM, and the change in intracellular Ca concentration was measured. The difference between a maximum value and a minimum value in the intracellular Ca concentration change was determined, and retained as measurement data. When a response with addition of 100 nM $PGE_2$ was taken as 0% and a response with addition of a buffer was taken as 100%, the concentration causing 50% inhibition was determined as an $IC_{50}$ value. The test results of several compounds of the formula (I) are shown in Table 1 as below. Further, in the table, Ex represents Example numbers as described later.

TABLE 1

| Ex | $IC_{50}$ (nM) |
|---|---|
| 63 | 0.3 |
| 66 | 0.53 |
| 71 | 0.32 |
| 80 | 0.85 |
| 102 | 1.8 |
| 103 | 0.4 |
| 113 | 0.9 |
| 117 | 1.9 |

Test Example 2 Receptor Binding Test Using EP1 Receptor-Expressing Cells

A signal peptide (MKTIIALSYIFCLVFA: SEQ ID NO: 1) and a FLAG sequence (DYKDDDDK: SEQ ID NO: 2) were introduced at the N-terminal of rat EP1 receptor, followed by subcloning into an expression vector (product name: pCEP4, Invitrogen). HEK293EBNA cells (American Type Culture Collection) were transfected with the rat EP1 expression vector using a transfection reagent (product name: Fugene-6, Roche-Diagnostics), and then cultured for 2 days in a medium containing 10% FBS (product name: DMEM, Invitrogen) at 37° C. under 5% $CO_2$. After culturing, the cells were collected, treated with a cell lysate (20 mM Tris(hydroxymethyl) aminomethane (Tris) buffer pH 7.5, 5 mM ethylenediaminetetraacetic acid (EDTA)), and ultracentrifuged (23000 revolutions, 25 minutes×2) for rough preparation of a membrane sample.

A reaction liquid containing the prepared membrane sample (15 μg) and $^3H$-$PGE_2$ (150 μl, composition: 10 mM 2-(N-morpholino)ethanesulfonic acid (MES)/potassium hydroxide (KOH) pH 6.0, 1 mM EDTA, 10 mM magnesium chloride ($MgCl_2$), 0.02% 3-[(3-Cholamidopropyl)dimethylammonio]propanesulfonate (CHAPS)) was incubated at room temperature for 1 hour. The reaction was stopped with an ice-cooled buffer, and suction-filtering was performed under reduced pressure to trap the bound $^3H$-$PGE_2$ to a glass filter (product name: UNIFILTER-96, GF/B, PerkinElmer), so as to measure the radioactivity of the binding with a microplate scintillation counter (product name: TopCount, Packard) using Microscinti (product name: MICROSCINTI 20, PerkinElmer).

The dissociation constant (Kd) and the maximum binding amount (Bmax) were determined from Scatchard plotting ("Annals of the New York Academy of Science" (US), 1949, Vol. 51, p. 660). Nonspecific bindings were determined as bindings in the presence of an excess amount (2.5 μM) of label-free $PGE_2$. The assessment of the inhibitory action on $^3H$-$PGE_2$ binding by the compound was carried out by adding 2.5 nM $^3H$-$PGE_2$ and the compound.

The inhibition constant Ki (nM) for each compound was obtained using the following formula:

$$Ki=IC_{50}/(1+([C]/Kd))$$

In the formula, [C] represents the concentration of $^3H$-$PGE_2$ employed in the reaction system.

As a result, for example, the compound of Example 71 showed a Ki value of 0.47 M.

Test Example 3 Action on Rat with Acetic Acid-Induced Pollakiuria

The anti-pollakisuria action of the compound was assessed using a pathological model. It has been known that intravesical treatment with acetic acid in rat damages the bladder mucosa, thereby activating the afferent nerve transmitting nociceptive stimulus ("The Journal of Neuroscience", (US), December 1992, Vol. 12, No. 12, p. 4878-89). Since the pollakiuria condition is induced by intravesical treatment with acetic acid, it is possible to assess the therapeutic effects of the compound against the symptoms.

For the experiment, male Wistar rats (Charles River Laboratories) having weights ranging from 200 to 450 g were used. The urinary bladder was exteriorized by midline abdominal incision under pentobarbital anesthesia (50 mg/kg, i.p.), and residual urine in the bladder was removed with a syringe equipped with a 27 G needle. Thereafter, 0.5 to 0.7 mL of a 1% acetic acid solution was injected into the bladder and the wound was closed. Two days later, experimentation was carried out. Rats were placed in metabolic cages for acclimation for 1 hour, and then the test drug was orally administered. Immediately thereafter, change in the amount of urination was continuously measured for 6 hours. Total amount of urine was divided by total urination incidents to calculate the effective bladder capacity. As a result, it was noted that the effective bladder capacity of the group of which the bladders had been treated with acetic acid was decreased as compared to that of the sham-operated group, and thus showed pollakiuria condition. On the other hand, it was confirmed that there were compounds which improved the pollakiuria condition excellently at a minimum effective dose (MED) of 3 mg/kg among the compounds of the formula (I).

Test Example 4 Test on Cytochrome P450 (CYP) 3A4 Enzyme Inhibition (Evaluation of Drug Interaction)

(1) Inhibition Test I (Calculation of Inhibitory Activity I)

Using a 96-well plate, a substrate (midazolam), a test compound and human liver microsome (0.1 mg protein/ml) were incubated at 37° C. for 20 minutes in a 100 mM phosphate buffer containing 0.1 mM EDTA and 1 mM NADPH. Then, the reaction was stopped by adding an aqueous solution containing 80% acetonitrile. Thereafter, each sample was analyzed by LC/MS, and the inhibitory activity I was calculated using the following formula.

$$\text{Inhibitory Activity } I(\%)=100-V_{i,I}/V_{0,I}\times 100$$

$V_{i,I}$: Metabolic rate of substrate in the presence of the test compound at a known concentration in the inhibition test I $V_{0,I}$: Metabolic rate of substrate in the absence of the test compound in the inhibition test I (2) Inhibition Test II (Calculation of Inhibitory Activity II)

Using a 96-well plate, a test compound and human liver microsome (0.1 mg protein/ml) were incubated at 37° C. for 30 minutes in a total amount of 145 μl of 100 mM phosphate buffer (pH=7.4) containing 0.1 mM EDTA and 1 mM NADPH. Then, midazolam as the substrate was added thereto and incubated at 37° C. for 20 minutes. After the incubation, the reaction was stopped by adding an aqueous solution containing 80% acetonitrile. Thereafter, each sample was analyzed by LC/MS, and the inhibitory activity II was calculated using the following formula.

$$\text{Inhibitory Activity } II(\%)=100-V_{i,II}/V_{0,II}/(100\text{-inhibitory activity } I(\%))\times 100\times 100$$

$V_{i,II}$: Metabolic rate of substrate in the presence of the test compound at a known concentration in the inhibition test II $V_{0,II}$: Metabolic rate of substrate in the absence of the test compound in the inhibition test II The test results of several compounds of the formula (I) are shown in Table 2.

TABLE 2

| Ex | Inhibitory activity I (%) | Inhibitory activity II (%) |
|---|---|---|
| 102 | 1 | 0 |
| 103 | 12 | 7 |
| 117 | 3 | 5 |

From the above, it was confirmed that the CYP3A4-inhibiting action of the compound of the formula (I) is weak and it is believed that there is less concern that the compound of the formula (I) causes a drug interaction with a drug which is metabolized by CYP 3A4.

Test Example 5 Test on Metabolic Stability in Human Liver Microsome

Using a glass test tube, a test compound and human liver microsome (0.2 mg protein/ml) were incubated at 37° C. for 15 minutes in a 100 mM phosphate buffer (pH=7.4) containing 0.1 mM EDTA and 1 mM NADPH. Thereafter, the reaction was stopped by adding an aqueous solution containing 80% acetonitrile. Thereafter, each sample was analyzed by HPLC and the in vitro clearance (CLint) was calculated by an integration plot. The test results of several compounds of the formula (I) are shown in Table 3.

TABLE 3

| Ex | CLint (ml/min/kg) |
|---|---|
| 71 | 153 |
| 80 | 212 |
| 102 | 244 |
| 103 | 228 |
| 117 | 58 |

From the above, it is believed that the compound of the formula (I) has high metabolic stability in the human liver and is less likely to be affected by the liver first pass effect.

As a result of the above tests, it was confirmed that the compound of the formula (I) has a potent EP1 receptor antagonistic action and therefore excellently improves the pollakiuria condition, and that it has desirable properties as a pharmaceutical product in that it presents little concern of causing a drug interaction, that it has excellent metabolic stability, and the like. Therefore, it can be used for the treatment or the like of a lower urinary tract symptom or the like. Furthermore, it has been confirmed that some of the compound of the formula (I) has an excellent drug disposition and has an inhibitory action against the increased intraurethral pressure and the increased intravesical pressure, induced by Sulprostone which is an EP1/EP3 receptor agonist.

Examples of diseases that cause the "a lower urinary tract symptom" in the present invention include overactive bladder, benign prostatic hyperplasia, bladder neck contracture, cystitis, prostatitis, and the like.

The "a lower urinary tract symptom" in the present invention includes urinary storage symptoms such as diurnal urinary frequency, nocturia, urinary urgency, urinary urge incontinence, and the like, voiding symptoms such as weak urination, interrupted urine flow, delayed urination, and the like, post-urination symptoms such as residual urine sensation and the like, and genital or lower abdominal pain such as bladder pain, urethral pain, vulvar pain, scrotal pain, pelvic pain, and the like. Furthermore, urinary storage symptoms, voiding symptoms, and post-urination symptoms include urinary storage symptoms, voiding symptoms and post-urination symptoms associated with benign prostatic hyperplasia. In addition, urinary storage symptoms include urinary storage symptoms associated with overactive bladder, cystitis, and prostatitis.

The pharmaceutical composition containing one or two or more kinds of the compound of the formula (I) or a salt thereof as an active ingredient can be prepared in accordance with a generally used method, using an excipient which is usually used in the art, that is, a pharmaceutical excipient, a pharmaceutical carrier, or the like.

The administration can be carried out through any mode of oral administration via tablets, pills, capsules, granules, powders, liquid preparations, or the like, or parenteral administration via injections such as intraarticular, intravenous, intramuscular, or others, suppositories, eye drops, eye ointments, percutaneous liquid preparations, ointments, percutaneous patches, transmucosal liquid preparations, transmucosal patches, inhalations, and the like.

Regarding solid composition for oral administration, tablets, powders, granules, or the like are used. In such a solid composition, one or two or more active ingredients are mixed with at least one inactive excipient such as lactose, mannitol, glucose, hydroxypropylcellulose, microcrystalline cellulose, starch, polyvinyl pyrrolidone, magnesium aluminometasilicate, and/or the like. According to a conventional method, the composition may contain inactive additives such as lubricants such as magnesium stearate and the like, disintegrators such as sodium carboxymethyl starch and the like, stabilizers, and solubilizing agents. Tablets or pills may be coated with sugar coating, or with a film of gastric or enteric substance if necessary.

The liquid composition for oral administration includes pharmaceutically acceptable emulsions, solutions, suspensions, syrups, elixirs, or the like, and contains a generally used inert diluent, such as purified water or ethanol. In addition to the inert diluent, the liquid composition may contain adjuvants such as solubilizing agents, moistening agents, and suspending agents, sweeteners, flavors, aromatics, and antiseptics.

Injections for parenteral administration include sterile, aqueous or non-aqueous solutions, suspensions, or emulsions. As the aqueous solvent, for example, distilled water for injection or physiological saline is included. Examples of the non-aqueous solvent include propylene glycol, polyethylene glycol, vegetable oils such as olive oil and the like, alcohols such as ethanol and the like, Polysorbate 80 (Pharmacopeia), etc. Such a composition may further contain tonicity agents, antiseptics, moistening agents, emulsifying agents, dispersing agents, stabilizers, or solubilizing agents. These are sterilized, for example, by filtration through a bacteria-retaining filter, blending with bactericides, or irradiation. In addition, these can also be used by producing sterile solid compositions, and dissolving or suspending it in sterile water or a sterile solvent for injection prior to their use.

Agents for external use includes ointments, plasters, creams, jellies, cataplasms, sprays, lotions, eye drops, eye ointments and the like. Generally used ointment bases, lotion bases, aqueous or non-aqueous liquid preparations, suspensions, emulsions and the like are included. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate and the like.

Regarding transmucosal agents such as inhalations, transnasal agents, and the like, in solid, liquid or semi-solid state are used, and can be prepared in accordance with conventionally known methods. For example, known excipients, as well as pH adjusting agents, antiseptics, surfactants, lubricants, stabilizers, thickeners, or the like may be appropriately added thereto. For their administration, appropriate devices for inhalation or insufflation may be used. For example, a compound may be administered alone or as powders of formulated mixture, or as solution or suspension by combining it with pharmaceutically acceptable carriers, using conventionally known devices or sprayers, such as a measured administration inhalation device and the like. The dry powder inhalers or the like may be for single or multiple administration use, and dry powders or powder-containing capsules may be used. Alternatively, this may be in a form of a pressurized aerosol spray which uses an appropriate propellant such as chlorofluoroalkane or hydrofluoroalkane, or a suitable gas such as carbon dioxide, or the like.

In the case of oral administration, it is appropriate that the daily dose may be usually from about 0.001 to 100 mg/kg, preferably from 0.1 to 30 mg/kg, and more preferably 0.1 to 10 mg/kg per body weight, and this is administered in a single portion or divided into 2 to 4 portions. Also, in the case of intravenous administration, the daily dose is from about 0.0001 to 10 mg/kg per body weight, and administration is made once a day or two or more times a day. In addition, a transmucosal agent is administered at a dose from about 0.001 to 100 mg/kg per body weight, once a day or two or more times a day. The dose is appropriately determined in response to an individual case by taking the symptoms, age, and sex, and the like into consideration.

The compound of formula (I) can be used in combination with various therapeutic agents or prophylactic agents for the diseases, in which the compound of the formula (I) is considered effective, as described above. The combined preparation may be administered simultaneously, or separately and continuously or at a desired time interval. The preparations to be co-administered may be a blend, or prepared individually.

EXAMPLE

Hereinbelow, the production processes for the compound (I) will be described in more detail with reference to Examples. Further, the present invention is not limited to the compounds described in the Examples as described below. Furthermore, the production processes for the starting compounds will be described in Preparative Examples. Further, the production processes for the compound of formula (I) are not limited to the production processes of the specific Examples as below, but the compound of formula (I) can be prepared by any combination of the production processes or the methods that are apparent to a person skilled in the art.

In addition, the following abbreviations may be used sometimes in Examples, Preparative Examples, and Tables as described later.

Pre: Preparative Example number, Ex: Example number, Str: Structural formula, Syn: production process (the numeral shows that it was prepared using a corresponding starting material in the same manner for an Example compound having its number as the Example number. Further, when P is prefixed before the number, it shows that the compound was prepared using a corresponding starting material in the same manner for the Preparative Example compound having its number as the Preparative Example number. Also, for example, when plural production processes as 1,6 are described, it shows that the compound was prepared using a corresponding starting material by sequentially performing the reactions from the left side). Dat: Physicochemical data (EI: EI-MS ([M]$^+$); EP: ESI-MS (Pos) (in a case of no description, [M+H]$^+$); EN: ESI-MS (Neg) ([M−H]$^-$); AP: APCI-MS (Pos) (in a case of no description, [M+H]$^+$); FP: FAB-MS (Pos) (in a case of no description, [M+H]$^+$); FN: FAB-MS (Neg) (in a case of no description, [M−H]$^-$); NMR1: δ (ppm) of the peaks in $^1$H-NMR in DMSO-d$_6$; NMR2: δ (ppm) of the peaks in $^1$H-NMR in CDCl$_3$; Me: Methyl, Et: Ethyl, F$_3$C: Trifluoromethyl, Boc: tert-Butoxycarbonyl, TBDPS: tert-Butyldiphenylsilyl.

Preparative Example 1

5.40 g of ethyl 5-methylpyrazine-2-carboxylate was dissolved in 54.0 mL of carbon tetrachloride, and 5.78 g of 1-bromosuccinimide and 267 mg of 2,2'-azobis(isobutyronitrile) were added thereto, followed by heating with reflux for 3 hours. The reaction liquid was left to be cooled to room temperature and then concentrated under reduced pressure, and the obtained residue was suspended in 100 mL of ethyl acetate and the insoluble materials were separated by filtration. The filtrate was washed with a saturated aqueous sodium hydrogen carbonate solution, water, and saturated brine, and then dried over anhydrous magnesium sulfate. The solvent was evaporated and the obtained residue was purified by silica gel column chromatography (hexane:ethyl acetate=4:1 to 1:1) to obtain 2.62 g of ethyl 5-(bromomethyl)pyrazine-2-carboxylate.

Preparative Example 2

3.88 g of 6-aminoindan-5-ol was dissolved in 80.0 mL of THF and 80.0 mL of water, and 5.21 g of sodium hydroxide and 22.8 g of di-tert-butyl bicarbonate were added thereto under ice-cooling, followed by stirring overnight at room temperature. The reaction liquid was concentrated under reduced pressure, and the obtained solution was adjusted to pH 5 by adding 0.1 M aqueous hydrochloric acid solution, followed by extraction with ethyl acetate. The organic layer was washed with water and saturated brine, and then dried over anhydrous magnesium sulfate. The solvent was evaporated and the obtained residue was purified by silica gel column chromatography (hexane:ethyl acetate=4:1) to obtain 3.36 g of tert-butyl (6-hydroxy-2,3-dihydro-1H-inden-5-yl) carbamate.

Preparative Example 3

1.00 g of tert-butyl (6-hydroxy-2,3-dihydro-1H-inden-5-yl)carbamate was dissolved in 10.0 mL of DMF, and 1.08 g of ethyl 5-(bromomethyl)pyrazine-2-carboxylate and 721 mg of potassium carbonate were added thereto, followed by stirring at 60° C. for 1 hour. The reaction liquid was poured into a 5% w/v aqueous citric acid solution, followed by extraction with ethyl acetate. The organic layer was washed with a 5% w/v aqueous citric acid solution, water, and saturated brine, and then dried over anhydrous magnesium sulfate. The solvent was evaporated and the obtained residue was purified by silica gel column chromatography (hexane:ethyl acetate=9:1 to 7:3) to obtain 690 mg of ethyl 5-[({6-[(tert-butoxycarbonyl)amino]-2,3-dihydro-1H-inden-5-yl}oxy)methyl]pyrazine-2-carboxylate.

Preparative Example 4

690 mg of ethyl 5-[({6-[(tert-butoxycarbonyl)amino]-2,3-dihydro-1H-inden-5-yl}oxy)methyl]pyrazine-2-carboxylate was dissolved in 7.00 mL of ethyl acetate, and 4.17 mL of a 4 M hydrogen chloride/ethyl acetate solution was added thereto, followed by stirring at 50° C. for 3 hours. The reaction liquid was concentrated under reduced pressure, and the obtained residue was solidified by the addition of isopropanol to obtain 712 mg of ethyl 5-{[(6-amino-2,3-dihydro-1H-inden-5-yl)oxy]methyl}pyrazine-2-carboxylate trihydrochloride.

Preparative Example 5

To 712 mg of ethyl 5-{[(6-amino-2,3-dihydro-1H-inden-5-yl)oxy]methyl}pyrazine-2-carboxylate trihydrochloride were added 35.6 mL of pyridine and 35.0 mL of a 0.21 M 4-methyl-1,3-thiazole-2-sulfonyl chloride/tert-butyl methyl ether solution, followed by stirring overnight at room temperature. The reaction liquid was concentrated under reduced pressure, and to the obtained residue was added a 5% w/v aqueous citric acid solution, followed by extraction with ethyl acetate. The organic layer was washed with water and saturated brine, and then dried over anhydrous magnesium sulfate. The solvent was evaporated and the obtained residue was purified by silica gel column chromatography (chloroform:methanol=100:1 to 95:5) to obtain 256 mg of ethyl 5-{[(6-{[(4-methyl-1,3-thiazol-2-yl)sulfonyl]amino}-2,3-dihydro-1H-inden-5-yl)oxy]methyl}pyrazine-2-carboxylate.

Preparative Example 6

2.13 g of tert-butyl (2-hydroxy-4,5-dimethylphenyl)carbamate was dissolved in 44.9 mL of THF, and 1.50 g of methyl 6-(hydroxymethyl)nicotinate, 7.06 g of triphenylphosphine, and 11.7 g of diethyl azodicarboxylate were added thereto, followed by stirring overnight at room temperature. To the reaction liquid was added a saturated aqueous sodium hydrogen carbonate solution, followed by extraction with ethyl acetate. The organic layer was washed with saturated brine and then dried over anhydrous sodium sulfate. The solvent was evaporated and the obtained residue was dissolved in 30.0 mL of ethyl acetate, and 60.0 mL of a 4 M hydrogen chloride/ethyl acetate solution was added thereto, followed by stirring for 1 hour. The resulting precipitate was collected by filtration, washed with ethyl acetate, and then dried under reduced pressure to obtain 1.76 g of methyl 6-[(2-amino-4,5-dimethylphenoxy)methyl]nicotinate hydrochloride.

Preparative Example 7

680 mg of methyl 4-({4,5-dimethyl-2-[(pyridin-2-ylsulfonyl)amino]phenoxy}methyl)benzoate was dissolved in 6.45 mL of pyridine, and 1.13 mL of 2-methyloxirane was added thereto, followed by stirring at 80° C. overnight in a sealed tube. The reaction liquid was concentrated under reduced pressure and the obtained residue was purified by silica gel column chromatography (chloroform:methanol=100:1 to 99:1) to obtain 466 mg of methyl 4-({2-[(2-hydroxypropyl)(pyridin-2-ylsulfonyl)amino]-4,5-dimethylphenoxy}methyl)benzoate.

Preparative Example 8

15.4 g of 2-fluoro-4-methylbenzoic acid was dissolved in 200 mL of methanol, and 10.0 mL of concentrated sulfuric acid was added thereto, followed by heating with reflux overnight. The reaction liquid was cooled to room temperature and then concentrated to about 50 mL, and water was added thereto, followed by extraction with ethyl acetate. The organic layer was washed with water and saturated brine, and then dried over anhydrous magnesium sulfate. The solvent was evaporated, and the obtained residue was purified by silica gel column chromatography (hexane:ethyl acetate=95:5 to 90:10) to obtain 15.2 g of methyl 2-fluoro-4-methylbenzoate.

Preparative Example 9

7.17 g of 6-nitroindan-5-ol was dissolved in 80.0 mL of DMF, and 10.9 g of methyl 4-(bromomethyl)-2-fluorobenzoate and 6.63 g of potassium carbonate were added thereto, followed by stirring at 50° C. overnight. To the reaction liquid was added water, followed by extraction with ethyl acetate, and the organic layer was washed with saturated brine and then dried over anhydrous magnesium sulfate. The solvent was evaporated and the obtained residue was purified by silica gel column chromatography (hexane:ethyl acetate=2:1 to 1:1) to obtain 11.1 g of methyl 2-fluoro-4-{[(6-nitro-2,3-dihydro-1H-inden-5-yl)oxy]methyl}benzoate.

Preparative Example 10

11.0 g of methyl 2-fluoro-4-{[(6-nitro-2,3-dihydro-1H-inden-5-yl)oxy]methyl}benzoate was dissolved in 120 mL of acetic acid and 12.0 mL of water, and 8.89 g of reduced iron was added thereto at 60° C., followed by stirring at 60° C. for 4.5 hours. The reaction liquid was cooled to room temperature, and then filtered through Celite, and the filtrate was concentrated under reduced pressure. The obtained residue was suspended in water and ethyl acetate, neutralized by the addition of sodium hydrogen carbonate, and then filtered through Celite. After the filtrate was extracted with ethyl acetate, the organic layer was washed with saturated brine and dried over anhydrous magnesium sulfate. The solvent was evaporated and the obtained residue was purified by silica gel column chromatography (toluene:ethyl acetate=95:5 to 90:10) to obtain 6.06 g of methyl 4-{[(6-amino-2,3-dihydro-1H-inden-5-yl)oxy]methyl}-2-fluorobenzoate.

Preparative Example 11

1.04 g of 55% sodium hydride/paraffin oil was suspended in 40.0 mL of DMF, and a solution of 3.90 g of 6-nitroindan-5-ol in DMF (10.0 mL) was added dropwise thereto at 5° C. over 15 minutes, followed by stirring at 5° C. for 30 minutes. To the reaction liquid was added dropwise 2.15 mL of methoxymethyl chloride over 5 minutes, followed by stirring at room temperature for 1 hour. To the reaction liquid was added water, followed by extraction with ethyl acetate, and the organic layer was washed with water and saturated brine, and then dried over anhydrous magnesium sulfate. The solvent was evaporated and the obtained residue was purified by silica gel column chromatography (hexane:ethyl acetate=100:0 to 80:20) to obtain 4.20 g of 5-(methoxymethoxy)-6-nitroindane.

Preparative Example 12

4.20 g of 5-(methoxymethoxy)-6-nitroindane was dissolved in 42.0 mL of methanol, and 500 mg of 10% palladium carbon was added thereto, followed by stirring at room temperature for 6 hours under a hydrogen atmosphere. After the catalyst was removed by filtration, the filtrate was concentrated under reduced pressure, and the obtained residue was purified by silica gel column chromatography (hexane:ethyl acetate=4:1) to obtain 3.30 g of 6-(methoxymethoxy)indan-5-amine.

Preparative Example 13

3.30 g of 6-(methoxymethoxy)indan-5-amine was dissolved in 33.0 mL of pyridine and 157 mL of a 0.54 M 4-methyl-1,3-thiazole-2-sulfonylchloride/tert-butyl methyl ether solution was added thereto, followed by stirring overnight at room temperature. The reaction liquid was concentrated under reduced pressure, to the residue were added water and ethyl acetate, and the insoluble materials were removed by filtration. After the filtrate was extracted with ethyl acetate, the organic layer was washed with water and saturated brine, and then dried over anhydrous magnesium sulfate. The solvent was evaporated and the obtained residue was purified by silica gel column chromatography (hexane:ethyl acetate=73:27 to 60:40) to obtain 4.79 g of N-[6-(methoxymethoxy)-2,3-dihydro-1H-inden-5-yl]-4-methyl-1,3-thiazole-2-sulfonamide.

Preparative Example 14

896 mg of N-[6-(methoxymethoxy)-2,3-dihydro-1H-inden-5-yl]-4-methyl-1,3-thiazole-2-sulfonamide, 665 mg of tributyl phosphine, and 257 mg of (2S)-2-fluoropropan-1-ol were dissolved in 8.96 mL of THF, and 829 mg of 1,1'-[(E)-diazen-1,2-diyldicarbonyl]dipiperidine was added thereto, followed by stirring overnight at room temperature. After the insoluble materials were removed by filtration, the filtrate was concentrated under reduced pressure, and the obtained residue was purified by silica gel column chromatography (hexane:ethyl acetate=90:10 to 50:50) to obtain 632 mg of N-[(2S)-2-fluoropropyl]-N-[6-(methoxymethoxy)-2,3-dihydro-1H-inden-5-yl]-4-methyl-1,3-thiazole-2-sulfonamide.

Preparative Example 15

630 mg of N-[(2S)-2-fluoropropyl]-N-[6-(methoxymethoxy)-2,3-dihydro-1H-inden-5-yl]-4-methyl-1,3-thiazole-2-sulfonamide was dissolved in 3.50 mL of methanol, and 1.50 mL of a 4 M hydrogen chloride/dioxane solution was added thereto, followed by stirring at room temperature for 6 hours. The reaction liquid was concentrated under reduced pressure, and to the obtained residue was added a saturated aqueous sodium hydrogen carbonate solution, followed by extraction with ethyl acetate. The organic layer was washed with saturated brine, and dried over anhydrous sodium sulfate, and then the solvent was evaporated to obtain 586 mg of N-[(2S)-2-fluoropropyl]-N-(6-hydroxy-2,3-dihydro-1H-inden-5-yl)-4-methyl-1,3-thiazole-2-sulfonamide.

Preparative Example 16

1.15 g of ethyl pyrazine-3,6-dicarboxylate was dissolved in 34.5 mL of ethanol, and 5.64 mL of a 1 M aqueous sodium hydroxide solution was added thereto, followed by stirring at room temperature for 3.5 hours. The precipitated salt was collected by filtration and dissolved in a small amount of water, and then this solution was acidified (pH=2) with a 1 M aqueous hydrochloric acid solution, followed by extraction with ethyl acetate. The organic layer was washed with saturated brine and dried over anhydrous sodium sulfate, and then the solvent was evaporated to obtain 435 mg of 6-(ethoxycarbonyl)pyridazine-3-carboxylic acid.

Preparative Example 17

435 mg of 6-(ethoxycarbonyl)pyridazine-3-carboxylic acid was dissolved in 11.0 mL of dimethoxyethane, and 0.424 mL of 4-methylmorpholine and 0.531 ml, of isobutyl chloroformate were added thereto at 0° C. After stirring at 0° C. for 2 hours, a suspension of 294 mg of sodium borohydride in water (2.50 mL) was added to the reaction liquid, followed by further stiffing at 0° C. for 20 minutes. To the reaction liquid was added water, followed by extraction with ethyl acetate, and the organic layer was washed with saturated brine and then dried over anhydrous magnesium sulfate. The solvent was evaporated and the obtained residue was purified by silica gel column chromatography (chloroform:methanol=97:3 to 90:10) to obtain 184 mg of ethyl 6-(hydroxymethyl)pyridazine-3-carboxylate.

Preparative Example 18

596 mg of methyl 4-({4,5-dimethyl-2-[(pyridin-2-ylsulfonyl)amino]phenoxy}methyl)benzoate was dissolved in 5.96 mL of DMF, and 820 mg of {[(2S)-3-bromo-2-methylpropyl]oxy}(tert-butyl)diphenylsilane and 1.37 g of cesium carbonate were added thereto, followed by stiffing at 80° C. for 4 hours. To the reaction liquid was added water, followed by extraction with ethyl acetate. The organic layer was washed with water and saturated brine, and then dried over anhydrous sodium sulfate. The solvent was evaporated and the obtained residue was purified by silica gel column chromatography (hexane:ethyl acetate=60:40) to obtain 840 mg of methyl 4-[(2-{[(2R)-3-{[tert-butyl(diphenyl)silyl]oxy}-2-methylpropyl](pyridin-2-ylsulfonyl)amino}-4,5-diphenylphenoxy)methyl]benzoate.

Preparative Example 19

840 mg of methyl 4-[(2-{[(2R)-3-{[tert-butyl(diphenyl)silyl]oxy}-2-methylpropyl](pyridin-2-ylsulfonyl)amino}-4,5-diphenylphenoxy)methyl]benzoate was dissolved in 8.40 mL of THF, and 0.554 mL of a 1 M tetrabutyl ammonium fluoride/THF solution was added thereto at room temperature, followed by stirring at room temperature for 2 hours. To the reaction liquid was added a saturated aqueous sodium hydrogen carbonate solution, followed by extraction with ethyl acetate. The organic layer was washed with water and saturated brine, and then dried over anhydrous sodium sulfate. The solvent was evaporated and the obtained residue was purified by silica gel column chromatography (hexane:ethyl acetate=60:40 to 0:100) to obtain 468 mg of methyl 4-[(2-{[(2R)-3-hydroxy-2-methylpropyl](pyridin-2-ylsulfonyl)amino}-4,5-dimethylphenoxy)methyl]benzoate.

The compounds of Preparative Examples 20 to 40 shown in the table below were prepared in the same manner as the methods of Preparative Examples 1 to 19, using each of the corresponding starting materials. The structures, the production processes, and the physicochemical data of the compounds of Preparative Examples are shown in Tables 4 to 6.

Example 1

311 mg of methyl 4-{[(6-{[(4-methyl-1,3-thiazol-2-yl)sulfonyl]amino}-2,3-dihydro-1H-inden-5-yl)oxy]methyl}benzoate, 63.6 mg of 2-fluoro-1-propanol, and 356 mg of triphenylphosphine were dissolved in 4.0 mL of THF, and 591 mg of diethyl azodicarboxylate was added thereto under ice-cooling, followed by stirring at room temperature for 20 hours. The reaction liquid was concentrated under reduced pressure and the obtained residue was purified by silica gel column chromatography (hexane:ethyl acetate=100:0 to 60:40) to obtain 364 mg of methyl 4-{[(6-{(2-fluoropropyl)[(4-methyl-1,3-thiazol-2-yl)sulfonyl]amino}-2,3-dihydro-1H-inden-5-yl)oxy]methyl}benzoate.

Example 2

133 mg of N-[(2S)-2-fluoropropyl]-N-(6-hydroxy-2,3-dihydro-1H-inden-5-yl)-4-methyl-1,3-thiazole-2-sulfonamide, 94.4 mg of tributylphosphine, and 71.5 mg of ethyl 5-(hydroxymethyl)pyridine-2-carboxylate were dissolved in 1.33 mL of THF, and 118 mg of 1,1'-[(E)-diazene-1,2-diyldicarbonyl]dipiperidine was added thereto, followed by stirring overnight at room temperature. After the insoluble materials were removed by filtration, the solvent was concentrated under reduced pressure and the obtained residue was purified by silica gel column chromatography (hexane:ethyl acetate=80:20) to obtain 116 mg of ethyl 5-{[(6-{[(2S)-2-fluoropropyl][(4-methyl-1,3-thiazol-2-yl)sulfonyl]amino}-2,3-dihydro-1H-inden-5-yl)oxy]methyl}pyridine-2-carboxylate.

Example 3

137 mg of N-[(2S)-2-fluoropropyl]-N-(6-hydroxy-2,3-dihydro-1H-inden-5-yl)-4-methyl-1,3-thiazole-2-sulfonamide was dissolved in 1.05 mL of DMF, and 139 mg of ethyl 2-(bromomethyl)-1,3-thiazole-5-carboxylate and 102 mg of potassium carbonate were added thereto, followed by stirring at room temperature for 2 hours. To the reaction liquid was added water, followed by extraction with ethyl acetate. The organic layer was washed with water and saturated brine, and then dried over anhydrous sodium sulfate. The solvent was concentrated under reduced pressure and the obtained residue was purified by silica gel column chromatography (hexane: ethyl acetate=1:1) to obtain 154 mg of ethyl 2-{[(6-{[(2S)-2-fluoropropyl][(4-methyl-1,3-thiazol-2-yl)sulfonyl]amino}-2,3-dihydro-1H-inden-5-yl)oxy]methyl}-1,3-thiazole-5-carboxylate.

Example 4

460 mg of methyl 4-({2-[(2-hydroxypropyl)(pyridin-2-ylsulfonyl)amino]-4,5-dimethylphenoxy}methyl)benzoate was dissolved in 4.00 mL of dichloromethane, and 161 mg of diethylaminosulfur trifluoride was added dropwise thereto under ice-cooling, followed by stirring under ice-cooling for 30 minutes. To the reaction liquid was added water, followed by extraction with ethyl acetate, and the organic layer was dried over anhydrous magnesium sulfate. The solvent was concentrated under reduced pressure and the obtained residue was purified by silica gel column chromatography (hexane:ethyl acetate=3:1 to 1:1) to obtain 109 mg of methyl 4-({2-[(2-fluoropropyl)(pyridin-2-ylsulfonyl)amino]-4,5-dimethylphenoxy}methyl)benzoate.

Example 5

351 mg of methyl 4-{[(6-{(2-fluoropropyl)[(4-methyl-1,3-thiazol-2-yl)sulfonyl]amino}-2,3-dihydro-1H-inden-5-yl)oxy]methyl}benzoate was dissolved in 5.00 mL of THF and 5.00 mL of methanol, and 2.03 mL of a 1 M aqueous sodium hydroxide solution was added thereto, followed by stirring at 50° C. for 4 hours. The reaction liquid was concentrated under reduced pressure, to the obtained residue were added a 5% w/v aqueous citric acid solution and chloroform, and the organic layer was separated using a Phase Separate-filter manufactured by Isotute, and dried over anhydrous sodium sulfate. The solvent was evaporated and the obtained residue was dissolved in 5.00 mL of ethanol, and 0.765 mL of an aqueous sodium hydroxide solution was added thereto, followed by concentration under reduced pressure. The obtained crude product was crystallized by the addition of isopropanol/ethanol, collected by filtration, and dried under reduced pressure to obtain 268 mg of sodium 4-{[(6-{(2-fluoropropyl)[(4-methyl-1,3-thiazol-2-yl)sulfonyl]amino}-2,3-dihydro-1H-inden-5-yl)oxy]methyl}benzoate.

Example 6

148 mg of methyl 6-[({6-[(2-fluoropropyl)(pyridin-3-ylsulfonyl)amino]-2,3-dihydro-1H-inden-5-yl}oxy)methyl]nicotinate was dissolved in 3.00 mL of THF and 1.50 mL of methanol, and 1.50 mL of a 1 M aqueous sodium hydroxide solution was added thereto, followed by stirring overnight at room temperature. The reaction liquid was concentrated under reduced pressure, and to the obtained residue was added a 5% w/v aqueous citric acid solution, followed by extraction with chloroform. The organic layer was concentrated under reduced pressure, and the obtained crude product was crystallized by the addition of isopropanol/diisopropyl ether, collected by filtration, and dried under reduced pressure to obtain 79 mg of 6-[({6-[(2-fluoropropyl)(pyridin-3-ylsulfonyl)amino]-2,3-dihydro-1H-inden-5-yl}oxy)methyl]nicotinic acid.

Example 7

312 mg of 4-{[(6-{[(2S)-2-fluoropropyl](pyridin-3-ylsulfonyl)amino}-1-2,3-dihydro-1H-inden-5-yl)oxy]methyl}benzoic acid was dissolved in 4.00 mL of DMF, and 125 mg of 1,1'-carbonyldiimidazole was added thereto at room temperature. After stirring at room temperature for 1 hour, 79.6 mg of methane sulfonamide and 127 mg of 1,8-diazabicyclo[5,4,0]undec-7-ene were added thereto, followed by further stirring at room temperature for 18 hours. The reaction liquid was added with water and acidified (pH=1) by the addition of a 1 M aqueous hydrochloric acid solution, followed by extraction with ethyl acetate. The organic layer was washed with saturated brine and then dried over anhydrous magnesium sulfate. The solvent was evaporated and the obtained residue was purified by silica gel column chromatography (chloroform:methanol=97:3 to 95:5), and the obtained residue was solidified by the addition of ethyl acetate/hexane, collected by filtration, and dried under reduced pressure to obtain 278 mg of 4-{[(6-{[(2S)-2-fluoropropyl](pyridin-3-ylsulfonyl)amino}-2,3-dihydro-1H-inden-5-yl)oxy]methyl}-N-(methylsulfonyl)benzamide.

The compounds of Examples 8 to 121 shown in the tables below were prepared in the same manner as the methods of Examples 1 to 7. The structures of the compounds of Examples are shown in Tables 7 to 19, and the production processes, and the physicochemical data of the compounds of Examples are shown in Tables 20 to 24.

TABLE 4

| Pre | Syn | Str | Dat |
|---|---|---|---|
| 1 | P1 | (structure) | EP: 247 |
| 2 | P2 | (structure) | EP: 272 [M + Na]+ |
| 3 | P3 | (structure) | EP: 436 [M + Na]+ |
| 4 | P4 | (structure) 3HCl | EP: 314 |
| 5 | P5 | (structure) | EP: 475 |
| 6 | P6 | (structure) HCl | EP: 287 |
| 7 | P7 | (structure) | FP: 485 |
| 8 | P8 | (structure) | EI: 168 |

TABLE 4-continued

| Pre | Syn | Str | Dat |
|-----|-----|-----|-----|
| 9 | P9 | [2,3-dihydro-1H-inden-5-yloxy-methyl-2-fluoro-benzoate with NO2] | EI: 345 |
| 10 | P10 | [2,3-dihydro-1H-inden-5-yloxy-methyl-2-fluoro-benzoate with NH2] | EP: 316 |
| 11 | P11 | [indane-OCH2OMe with NO2] | EI: 223 |
| 12 | P12 | [indane-OCH2OMe with NH2] | EI: 193 |
| 13 | P13 | [indane-OCH2OMe with NHSO2-thiazole-Me] | EN: 353 |
| 14 | P14 | [indane-OCH2OMe with N(CH2CHMeF)SO2-thiazole-Me] | EP: 415 |
| 15 | P15 | [indane-OH with N(CH2CHMeF)SO2-thiazole-Me] | EP: 371 |
| 16 | P16 | [HO2C-pyridazine-CO2Et] | EP: 197 |

TABLE 5

| Pre | Syn | Str | Dat |
|-----|-----|-----|-----|
| 17 | P17 | [HO-CH2-pyridazine-CO2Et] | EP: 183 |

TABLE 5-continued

| Pre | Syn | Str | Dat |
|-----|-----|-----|-----|
| 18 | P18 | [dimethylphenyl-O-CH2-phenyl-CO2Me with N(CH2CHMeCH2OTBDPS)SO2-pyridine] | EP: 737 |
| 19 | P19 | [dimethylphenyl-O-CH2-phenyl-CO2Me with N(CH2CHMeCH2OH)SO2-pyridine] | EP: 499 |
| 20 | P5 | [dimethylphenyl-O-CH2-pyridine-CO2Me with NHSO2-pyridine] | EP: 428 |
| 21 | P5 | [dimethylphenyl-O-CH2-pyridine-CO2Me with NHSO2-furan-Me] | EP: 431 |
| 22 | P5 | [dimethylphenyl-O-CH2-pyridine-CO2Me with NHSO2-difluorophenyl] | EP: 463 |
| 23 | P6 | [indane-O-CH2-pyridine-CO2Et with NH2·HCl] | EP: 299 |
| 24 | P5 | [indane-O-CH2-pyridine-CO2Me with NHSO2-furan-Me] | EP: 443 |
| 25 | P5 | [indane-O-CH2-pyridine-CO2Me with NHSO2-pyridine] | EP: 440 |

TABLE 5-continued

| Pre | Syn | Str | Dat |
|---|---|---|---|
| 26 | P7 | | FP: 505 |
| 27 | P7 | | FP: 505 |
| 28 | P7 | | FP: 505 |

TABLE 6

| Pre | Syn | Str | Dat |
|---|---|---|---|
| 29 | P7 | | FP: 505 |
| 30 | P1 | | EI: 245 |
| 31 | P5 | | EP: 477 |
| 32 | P9 | | EI: 357 |
| 33 | P10 | | FP: 328 |
| 34 | P5 | | EP: 489 |
| 35 | P1 | | EP: 252 |
| 36 | P1 | | EP: 245 |
| 37 | P18 | | EP: 737 |
| 38 | P19 | | AP: 499 |
| 39 | P7 | | EP: 511 |
| 40 | P7 | | EP: 511 |

TABLE 7
| Ex | Str |
|---|---|
| 1 | 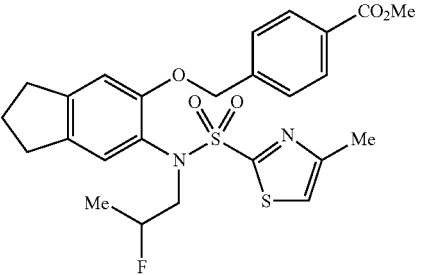 |
| 2 | 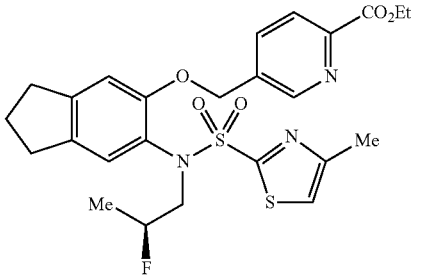 |
| 3 | 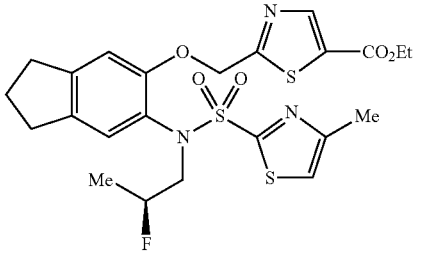 |
| 4 | 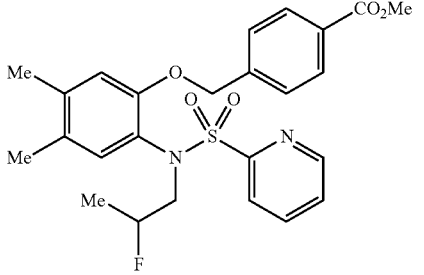 |
| 8 | 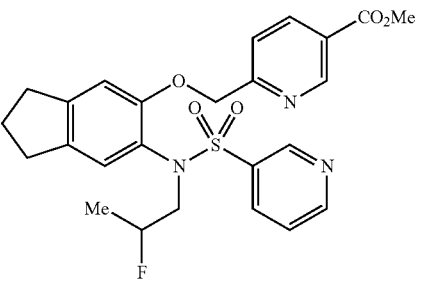 |
TABLE 7-continued
| Ex | Str |
|---|---|
| 9 | 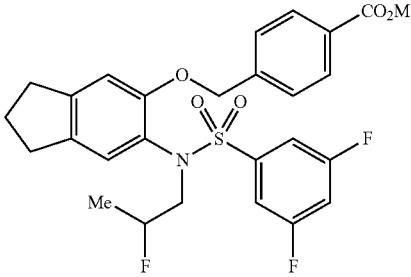 |
| 10 | 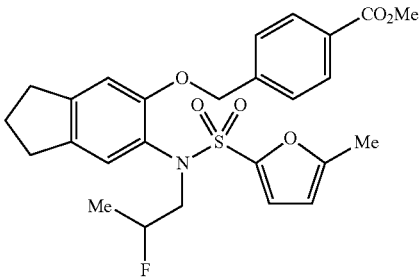 |
| 11 | 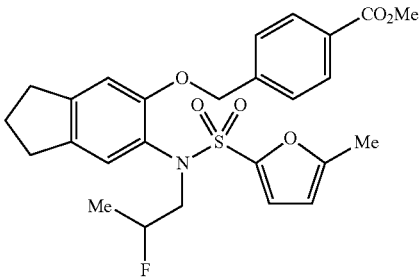 |
| 12 | 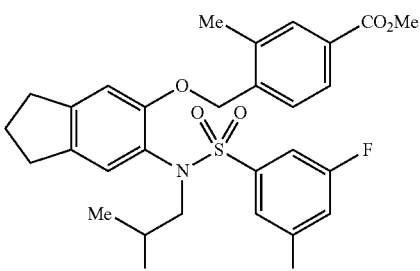 |
| 13 | 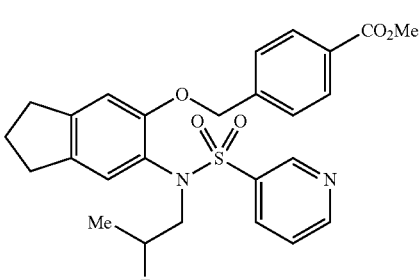 |

TABLE 8
| Ex | Str |
|---|---|
| 14 | |
| 15 | |
| 16 | |
| 17 | |
| 18 | |
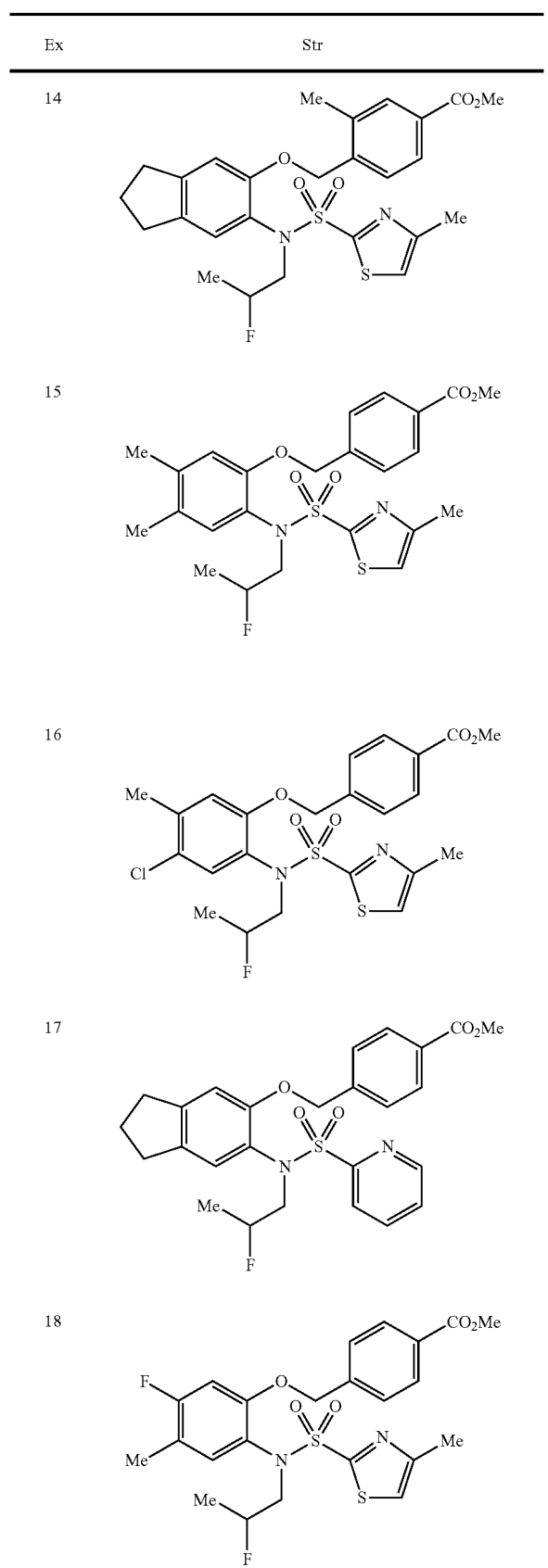
TABLE 8-continued
| Ex | Str |
|---|---|
| 19 | |
| 20 | |
| 21 | |
| 22 | |
| 23 | |
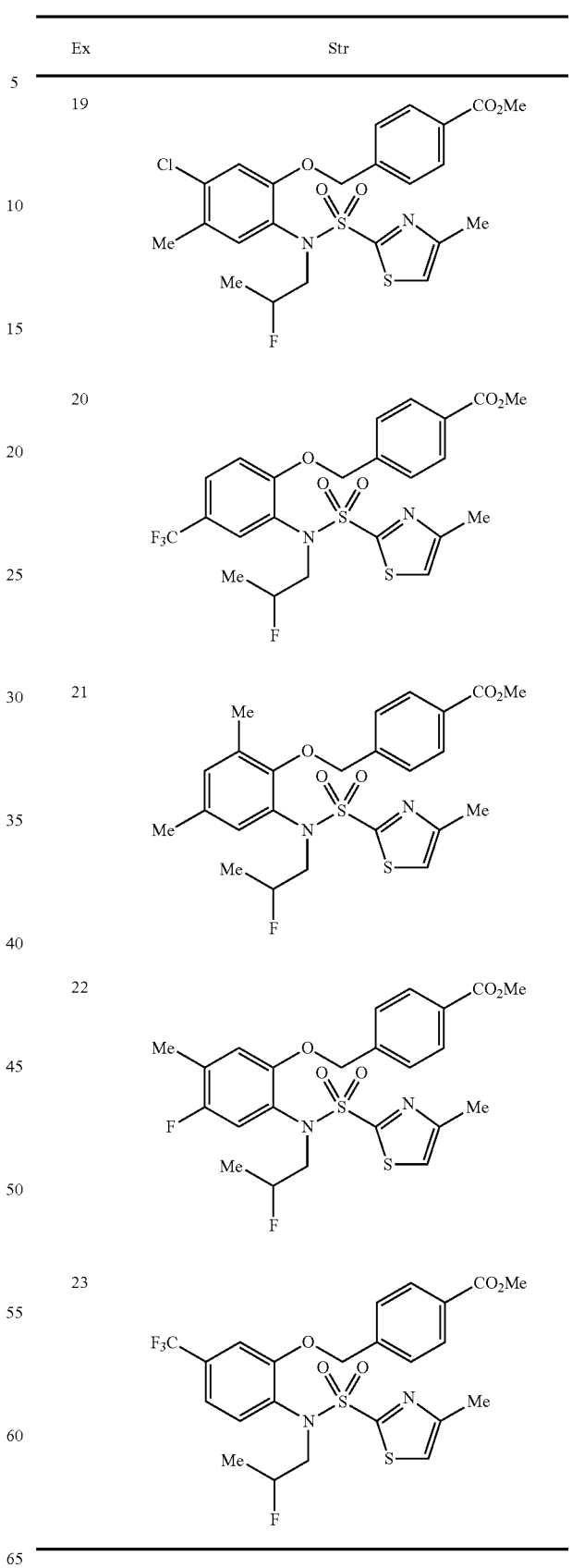

TABLE 9
| Ex | Str |
|---|---|
| 24 | 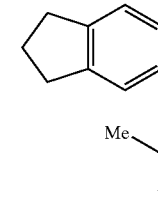 |
| 25 | |
| 26 | |
| 27 | |
| 28 | |
TABLE 9-continued
| Ex | Str |
|---|---|
| 29 | 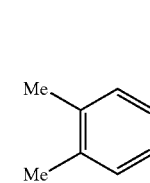 |
| 30 | |
| 31 | |
| 32 | |
| 33 | |

TABLE 10
| Ex | Str |
|---|---|
| 34 | |
| 35 | |
| 36 | |
| 37 | |
| 38 | |
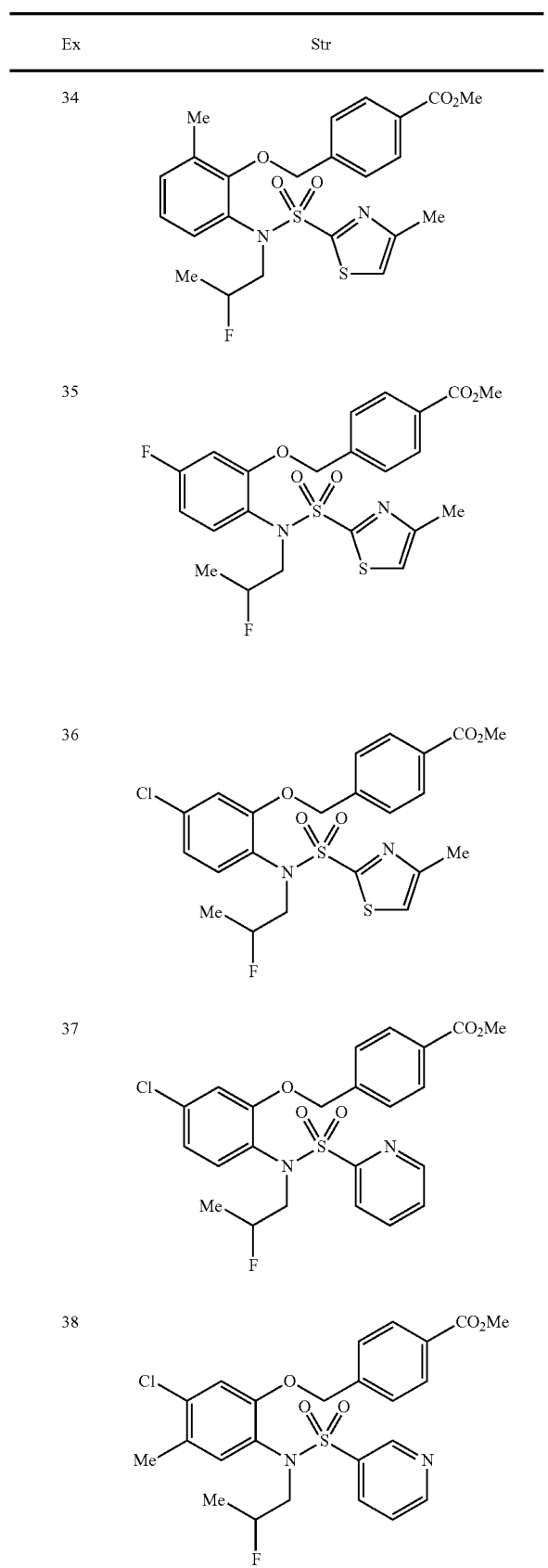
TABLE 10-continued
| Ex | Str |
|---|---|
| 39 | |
| 40 | |
| 41 | |
| 42 | |
| 43 | |
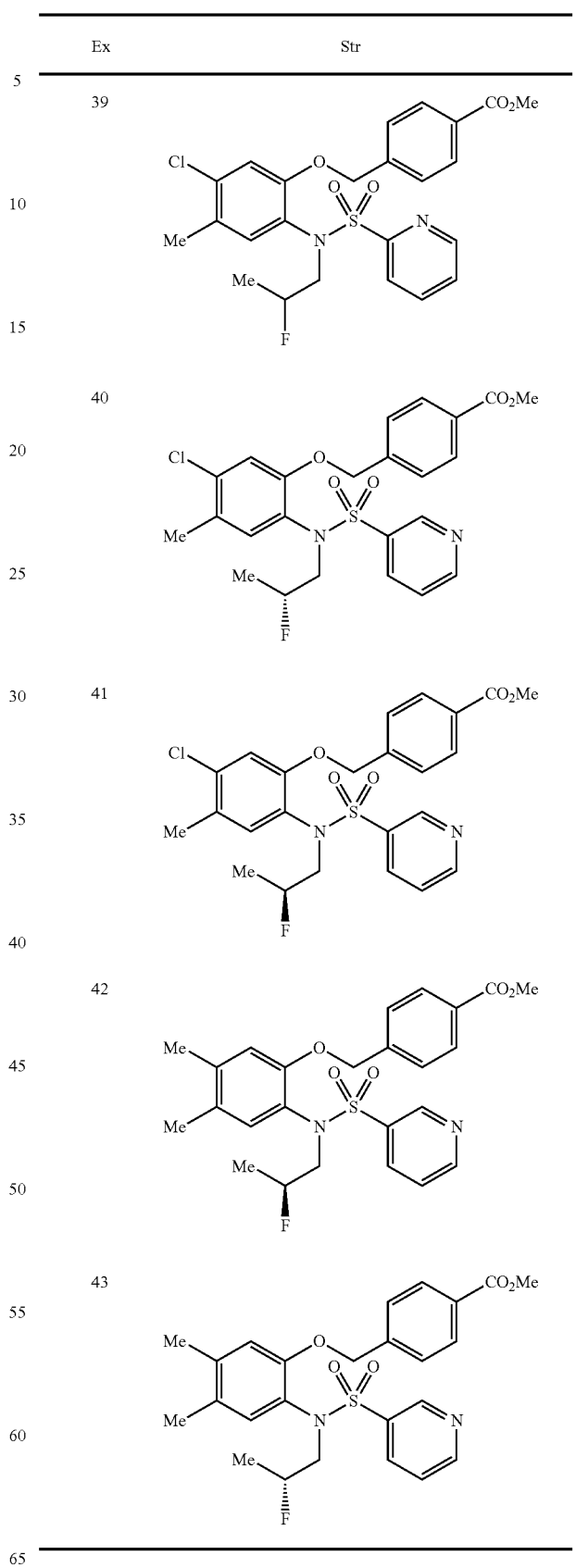

TABLE 11
| Ex | Str |
|---|---|
| 44 | |
| 45 | |
| 46 | |
| 47 | |
| 48 | |
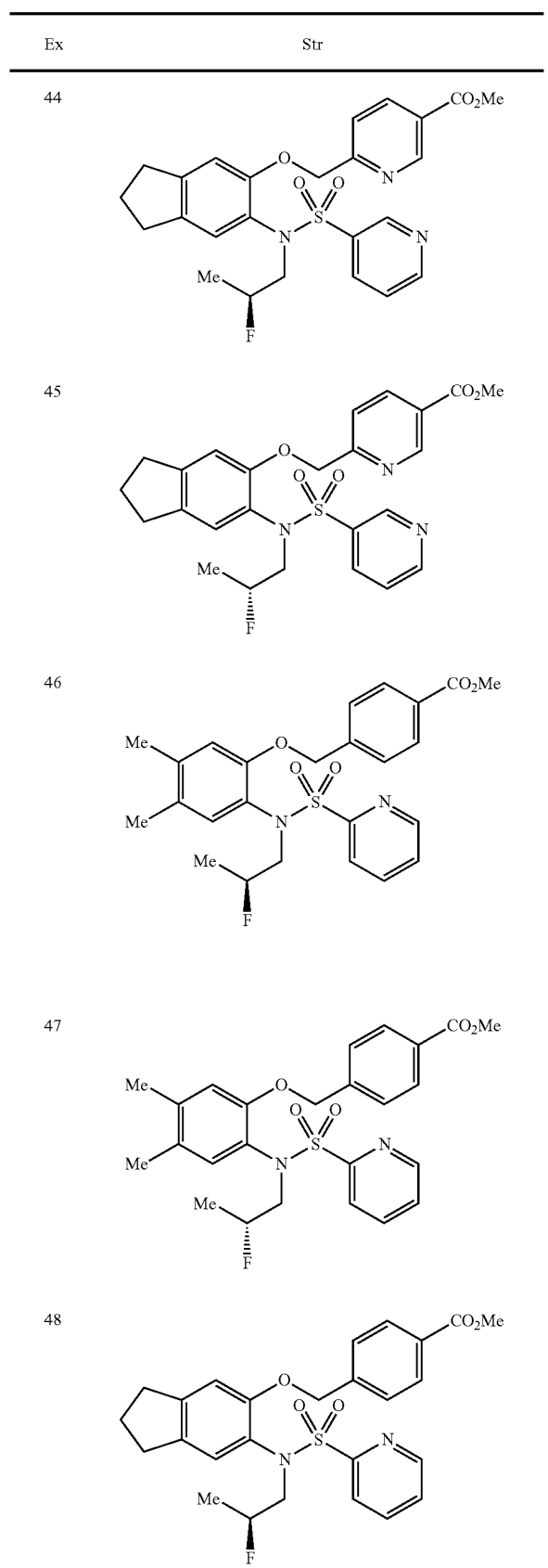
TABLE 11-continued
| Ex | Str |
|---|---|
| 49 | |
| 50 | |
| 51 | |
| 52 | |
| 53 | |
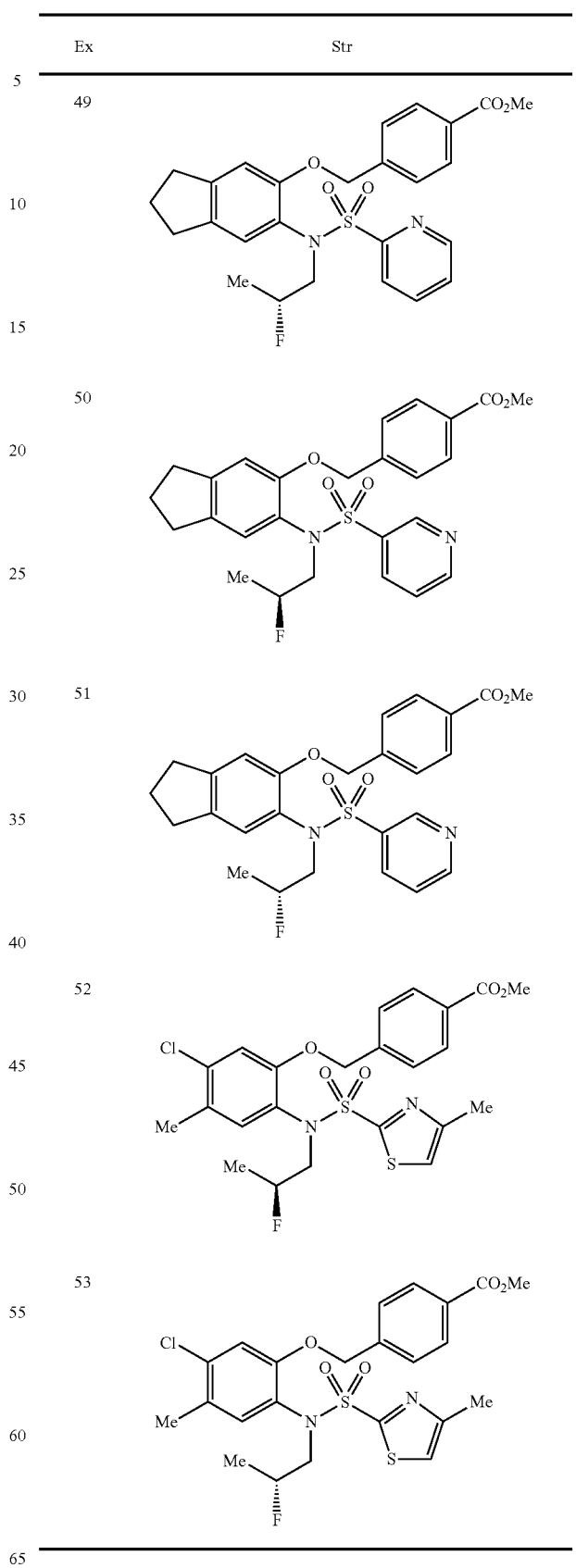

TABLE 12
| Ex | Str |
|---|---|
| 54 | 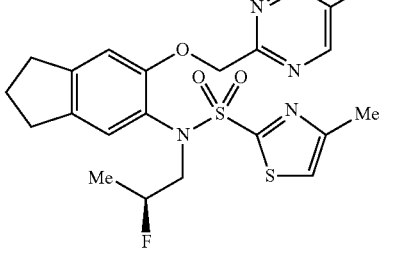 |
| 55 | 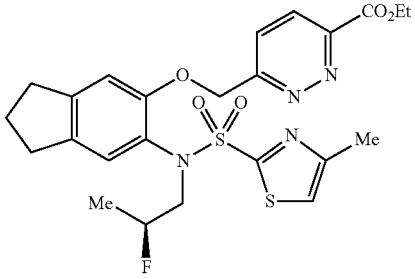 |
| 56 | 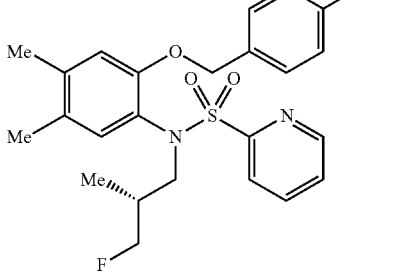 |
| 57 | 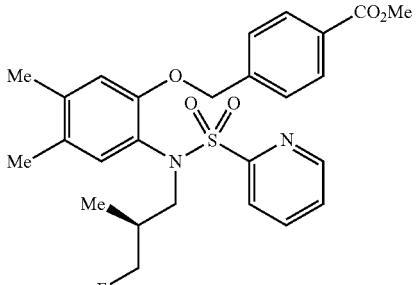 |
| 58 | 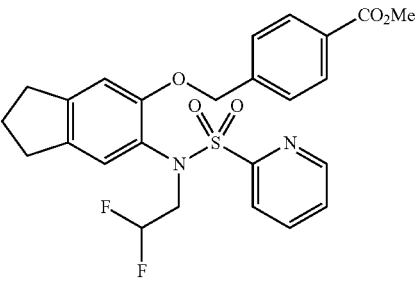 |
TABLE 12-continued
| Ex | Str |
|---|---|
| 59 | 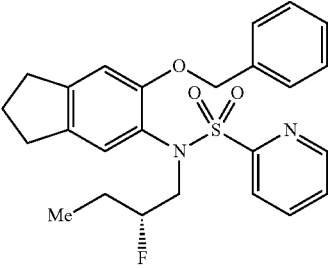 |
| 60 |  |
TABLE 13
| Ex | Str |
|---|---|
| 5 | 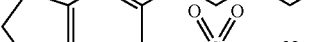 |
| 6 | 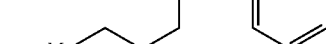 |
| 7 | 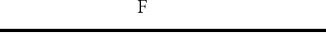 |

TABLE 13-continued

| Ex | Str |
|---|---|
| 61 | (structure) |
| 62 | (structure) |
| 63 | (structure) |
| 64 | (structure) |
| 65 | (structure) |因

TABLE 13-continued

| Ex | Str |
|---|---|
| 66 | (structure) |
| 67 | (structure) |

TABLE 14

| Ex | Str |
|---|---|
| 68 | (structure) |
| 69 | (structure) |
| 70 | (structure) |

TABLE 14-continued

| Ex | Str |
|---|---|
| 71 | (structure) |
| 72 | (structure) |
| 73 | (structure) |
| 74 | (structure) |
| 75 | (structure) |
| 76 | (structure) |
| 77 | (structure) |

TABLE 15

| Ex | Str |
|---|---|
| 78 | (structure) |
| 79 | (structure) |
| 80 | (structure) |

TABLE 15-continued
| Ex | Str |
|----|-----|
| 81 | 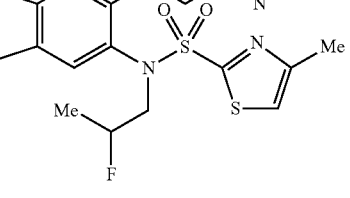 |
| 82 | |
| 83 | |
| 84 | |
| 85 | |
TABLE 15-continued
| Ex | Str |
|----|-----|
| 86 | 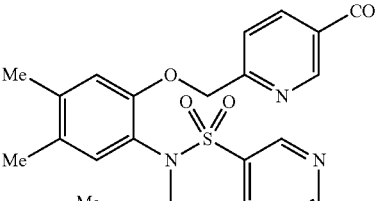 |
| 87 | |
TABLE 16
| Ex | Str |
|----|-----|
| 88 | 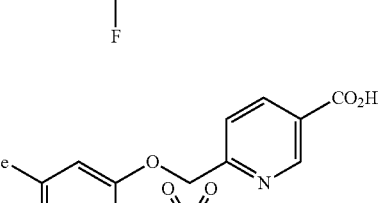 |
| 89 | |
| 90 | |

TABLE 16-continued

| Ex | Str |
|---|---|
| 91 | (structure) |
| 92 | (structure) |
| 93 | (structure) |
| 94 | (structure) |
| 95 | (structure) |
| 96 | (structure) |
| 97 | (structure) |

TABLE 17

| Ex | Str |
|---|---|
| 98 | (structure) |
| 99 | (structure) |
| 100 | (structure) |

TABLE 17-continued
| Ex | Str |
|---|---|
| 101 | 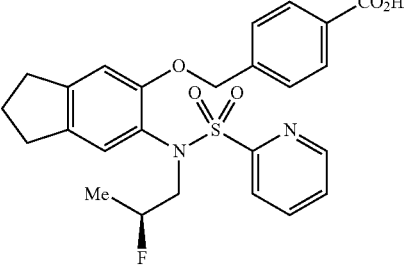 |
| 102 | 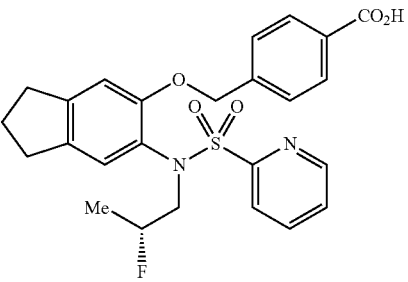 |
| 103 | 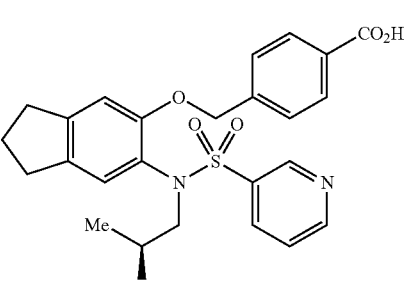 |
| 104 | 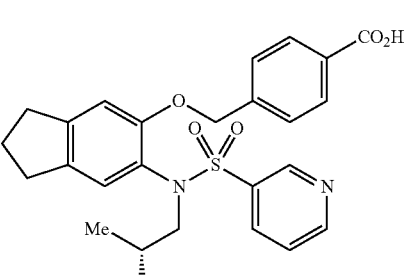 |
| 105 | 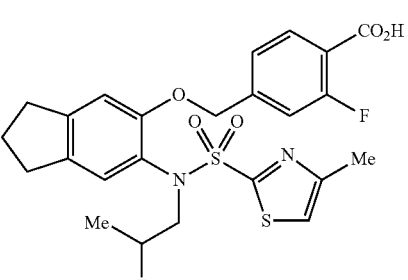 |
TABLE 17-continued
| Ex | Str |
|---|---|
| 106 | 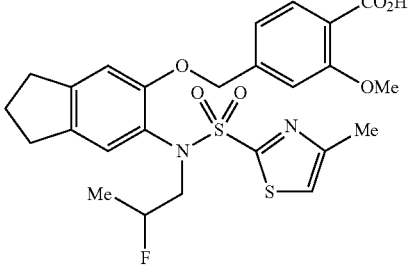 |
| 107 | 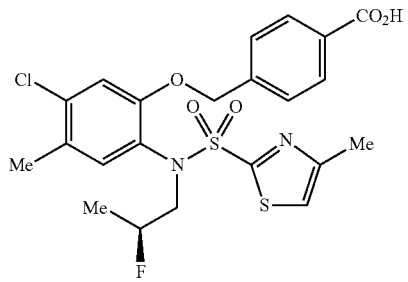 |
TABLE 18
| Ex | Str |
|---|---|
| 108 | 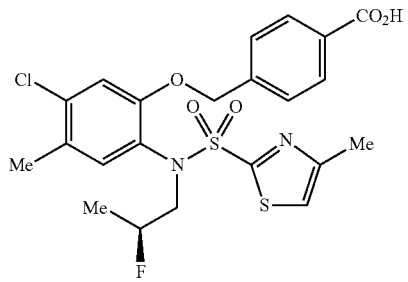 |
| 109 | 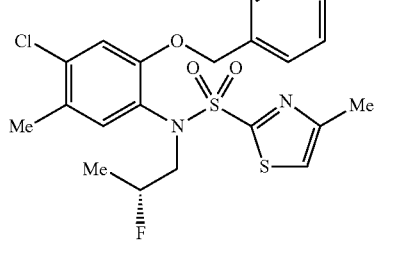 |
| 110 | 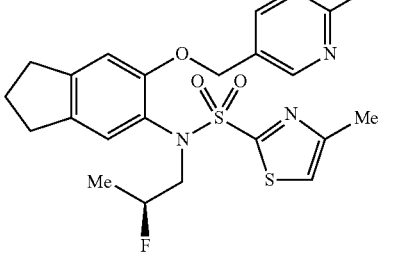 |

TABLE 18-continued
| Ex | Str |
|---|---|
| 111 | 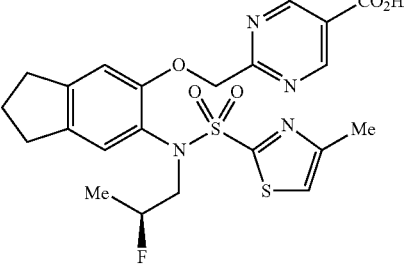 |
| 112 | 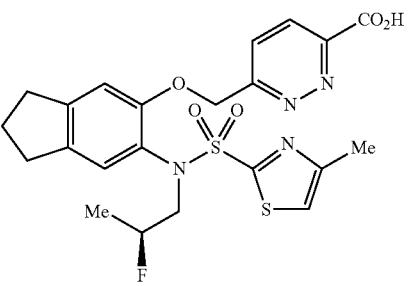 |
| 113 | 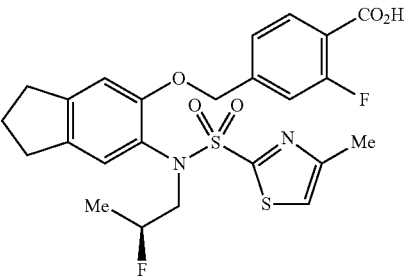 |
| 114 | 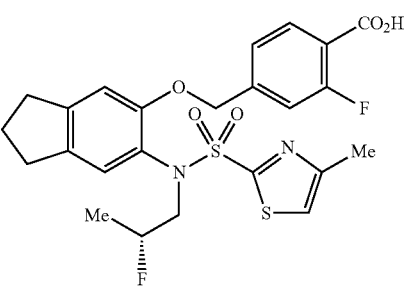 |
| 115 | 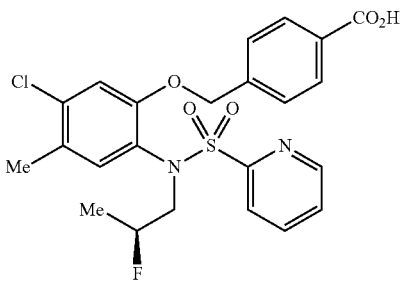 |
| 116 | 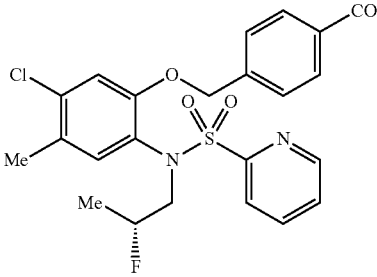 |
| 117 | 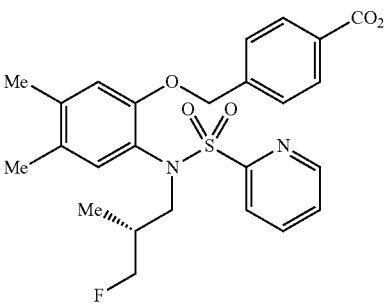 |
TABLE 19
| Ex | Str |
|---|---|
| 118 | 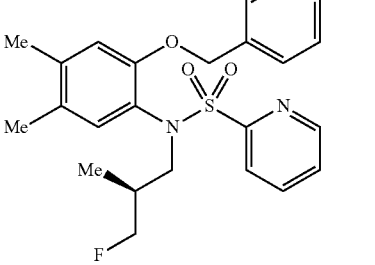 |
| 119 | 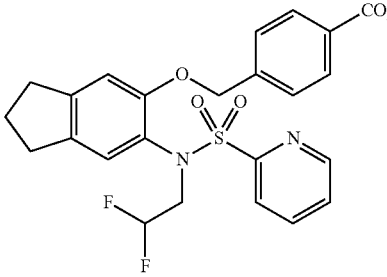 |
| 120 | 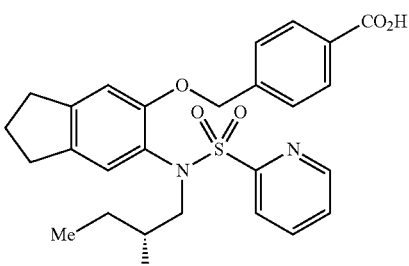 |

TABLE 19-continued

| Ex | Str |
|---|---|
| 121 | 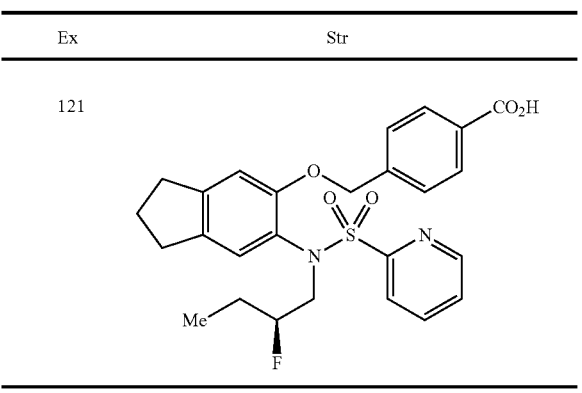 |

TABLE 20

| Ex | Syn | Dat |
|---|---|---|
| 1 | 1 | NMR2: 1.29-1.46 (3H, m), 1.96-2.17 (2H, m), 2.19-2.38 (3H, m), 2.72-2.94 (4H, m), 3.50-3.85 (1H, m), 3.85-4.00 (3H, m), 4.00-4.26 (1H, m), 4.53-5.16 (3H, br), 6.76 (1H, s), 6.91 (1H, s), 7.21 (1H, s), 7.23-7.36 (2H, m), 8.03 (2H, d, J = 9.0 Hz); FP: 519 |
| 2 | 2 | NMR2: 1.36 (3H, dd, J = 6.3, 23.6 Hz), 1.47 (3H, t, J = 7.1 Hz), 2.05-2.11 (2H, m), 2.33 (3H, brs), 2.83-2.90 (4H, m), 3.52-4.20 (2H, m), 4.51 (2H, q, J = 7.1 Hz), 4.57-5.18 (3H, m), 6.80 (1H, s), 6.95 (1H, brs), 7.16 (1H, s), 7.70-7.90 (1H, m), 8.16 (1H, d, J = 8.0 Hz), 8.64 (1H, s); EP: 534 |
| 3 | 3 | NMR2: 1.36-1.46 (6H, m), 2.04-2.11 (2H, m), 2.34 (3H, brs), 2.82-2.93 (4H, m), 3.58-3.45 (2H, m), 4.39 (2H, q, J = 7.1 Hz), 4.58-5.35 (3H, m), 6.79 (1H, s), 6.99 (1H, s), 7.24 (1H, s), 8.34 (1H, s); EP: 540 |
| 4 | 4 | FP: 487 |
| 5 | 5 | NMR1: 1.20-1.35 (3H, m), 1.97-2.08 (2H, m), 2.20 (3H, s), 2.72-2.92 (4H, m), 3.52-3.79 (1H, br), 3.79-4.12 (1H, br), 4.43-4.77 (2H, br), 4.77-5.03 (1H, br), 7.00 (1H, s), 7.05-7.14 (3H, m), 7.51 (1H, s), 7.84 (2H, d, J = 8.0 Hz); FP: 505 |
| 6 | 6 | NMR1: 1.29 (3H, dd, J = 6.2, 23.8 Hz), 1.95-2.05 (2H, m), 2.8-2.83 (4H, m) 3.65-5.03 (5H, m), 6.98 (1H, s), 7.09-7.25 (2H, m), 7.35-7.38 (1H, m), 7.96 (1H, dt, J = 1.4, 2 Hz), 8.22 (1H, d, J = 4.1 Hz), 8.57 (1H, brs), 8.71 (1H, s), 8.99 (1H, d, J = 1 Hz), 13.43 (1H, brs); FP: 486 |
| 7 | 7 | NMR1: 1.27 (3H, dd, J = 6.1, 23.8 Hz), 1.89-2.14 (2H, m), 2.72-2.98 (4H, m), 3.39 (3H, s), 3.47-4.15 (2H, m), 4.52-5.11 (3H, m), 6.97 (1H, s), 7.22 (2H, d, J = 7.7 Hz), 7.32-7.45 (1H, m), 7.89 (2H, d, J = 8.2 Hz), 7.94-7.97 (1H, s), 8.63 (1H, s), 8.67 (1H, d, J = 2.2 Hz), 12.14 (1H, brs); EP: 562 |
| 8 | 1 | EP: 500 |
| 9 | 1 | FP: 533 [M]+ |
| 10 | 1 | EP: 502 |
| 11 | 1 | EP: 548 |
| 12 | 1 | API: 499 |
| 13 | 1 | FP: 516 |
| 14 | 1 | FP: 533 |
| 15 | 1 | FP: 507 |
| 16 | 1 | FP: 527 [M]+ |
| 17 | 1 | EP: 499 |
| 18 | 1 | FP: 511 |
| 19 | 1 | FP: 527 [M]+ |
| 20 | 1 | FP: 547 |

TABLE 21

| Ex | Syn | Dat |
|---|---|---|
| 21 | 1 | FP: 507 [M]+ |
| 22 | 1 | FP: 511 |
| 23 | 1 | EP: 547 |
| 24 | 1 | FP: 487 |
| 25 | 1 | FP: 531 [M]+ |
| 26 | 1 | FP: 492 [M]+ |
| 27 | 1 | FP: 493 |
| 28 | 1 | EP: 539 [M]+ |
| 29 | 1 | EP: 535 [M]+ |
| 30 | 1 | FP: 488 |
| 31 | 1 | FP: 491 |
| 32 | 1 | EP: 523 |
| 33 | 1 | FP: 503 |
| 34 | 1 | FP: 493 |
| 35 | 1 | FP: 497 |
| 36 | 1 | EP: 513 [M]+ |
| 37 | 1 | EP: 493 [M]+ |
| 38 | 4 | FP: 507 |
| 39 | 4 | FP: 507 |
| 40 | 4 | FP: 507 |
| 41 | 4 | FP: 507 |
| 42 | 1 | FP: 487 |
| 43 | 1 | FP: 487 |
| 44 | 1 | EP: 500 |
| 45 | 1 | EP: 500 |
| 46 | 1 | FP: 487 |
| 47 | 1 | FP: 487 |
| 48 | 1 | EP: 499 |
| 49 | 1 | EP: 499 |
| 50 | 1 | EP: 499 |
| 51 | 1 | EP: 499 |
| 52 | 1 | EP: 527 |
| 53 | 1 | EP: 527 |
| 54 | 3 | EP: 535 |
| 55 | 2 | FP: 535 |
| 56 | 4 | EP: 501 |

TABLE 22

| Ex | Syn | Dat |
|---|---|---|
| 57 | 4 | EP: 501 |
| 58 | 1 | EP: 503 |
| 59 | 4 | EP: 513 |
| 60 | 4 | EP: 513 |
| 61 | 5 | NMR1: 1.16-1.34 (3H, m), 1.91-2.12 (2H, m), 2.74-2.92 (4H, m), 3.43-3.68 (1H, brs), 3.76-4.10 (1H, brs), 4.33-5.10 (3H, brs), 6.94-7.05 (3H, m), 7.09 (1H, s), 7.18-7.29 (2H, m), 7.32-7.43 (1H, m), 7.81 (2H, d, J = 8.0 Hz); FP: 520 |
| 62 | 5 | NMR1: 1.25 (3H, dd, J = 6.2, 23.8 Hz), 1.95-2.07 (2H, m), 2.48-2.53 (3H, m), 2.71-2.91 (4H, m), 3.49-4.01 (2H, br), 4.60-5.14 (3H, br), 6.14 (1H, dd, J = 0.8, 3.2 Hz), 6.82 (1H, d, J = 3.4 Hz), 7.00 (1H, s), 7.04 (1H, s), 7.18 (2H, d, J = 8.1 Hz), 7.84 (1H, d, J = 8.0 Hz); EP: 510 [M + Na]+ |
| 63 | 5 | NMR1: 1.23 (3H, dd, J = 6.0, 23.9 Hz), 1.98-2.09 (2H, m), 2.18 (3H, s), 2.76-2.94 (4H, m), 3.39-3.63 (1H, br), 3.72-4.09 (1H, br), 4.37-4.99 (3H, br), 6.86 (1H, d, J = 7.5 Hz), 7.09 (2H, s), 7.20-7.29 (2H, m), 7.32-7.42 (1H, m), 7.61 (1H, d, J = 7.9 Hz), 7.66 (1H, s); FP: 556 [M + Na]+ |
| 64 | 5 | FP: 485 |
| 65 | 6 | FP: 502 |
| 66 | 5 | NMR1: 1.25 (3H, dd, J = 4.7, 17.9 Hz), 1.98-2.09 (1H, m), 2.19 (3H, s), 2.21 (3H, s), 2.80 (2H, t, J = 5.4 Hz), 2.87 (2H, t, J = 5.6 Hz), 3.28-3.48 (1H, m), 3.50-4.10 (2H, m), 4.56-5.01 (4H, m), 7.02 (1H, d, J = 6.0 Hz), 7.08 (2H, s), 7.52 (1H, d, J = 0.7 Hz), 7.66 (1H, d, J = 6.0 Hz), 7.68 (1H, s); EP: 541 |
| 67 | 6 | FP: 493 |
| 68 | 5 | FP: 535 |
| 69 | 5 | FP: 485 |
| 70 | 5 | FP: 497 |
| 71 | 5 | NMR1: 1.27 (3H, dd, J = 6.2, 23.7 Hz), 2.19 (3H, s), 2.26 (3H, s), 3.48-4.20 (2H, m), 4.42-5.15 (3H, m), 7.08 (2H, d, J = 7.9 Hz), 7.23 (1H, s), 7.28 (1H, s), 7.53 (1H, s), 7.83 (2H, d, J = 7.9 Hz); FP: 513 |
| 72 | 5 | FP: 535 |
| 73 | 5 | EP: 493 |

TABLE 22-continued

| Ex | Syn | Dat |
|---|---|---|
| 74 | 5 | FP: 497 |
| 75 | 6 | FP: 535 |
| 76 | 5 | EP: 473 |
| 77 | 6 | EP: 517 [M]+ |
| 78 | 5 | FP: 479 |
| 79 | 5 | FP: 479 |

TABLE 23

| Ex | Syn | Dat |
|---|---|---|
| 80 | 5 | NMR1: 1.27 (3H, d, J = 6.4 Hz), 1.33 (3H, d, J = 6.4 Hz), 2.03 (2H, m), 2.16 (3H, s), 2.81 (2H, m), 2.86 (2H, m), 3.76 (1H, br), 4.01 (1H, br), 4.76 (1H, br), 5.01 (1H, br), 7.05 (1H, s), 7.11 (1H, br), 7.44 (1H, d, J = 1.0 Hz), 8.38 (1H, s), 8.95 (1H, d, J = 1.0 Hz); EP: 533 [M + Na]+ |
| 81 | 5 | NMR1: 1.23 (3H, d, J = 6.2 Hz), 1.29 (3H, d, J = 6.2 Hz), 2.02 (2H, m), 2.28 (3H, s), 2.80 (2H, m), 2.85 (2H, m), 3.64 (1H, br), 3.98 (1H, br), 4.68 (1H, br), 4.98 (1H, br), 6.78 (1H, d, J = 3.4 Hz), 7.03 (1H, s), 7.04 (1H, d, J = 3.4 Hz), 7.08 (1H, br), 7.52 (1H, s); EP: 529 [M + Na]+ |
| 82 | 6 | FP: 474 |
| 83 | 6 | FP: 477 |
| 84 | 6 | FP: 509 |
| 85 | 6 | FP: 489 |
| 86 | 6 | FP: 479 |
| 87 | 6 | FP: 483 |
| 88 | 6 | FP: 499 [M]+ |
| 89 | 6 | EP: 479 |
| 90 | 6 | FP: 473 |
| 91 | 5 | FP: 493 |
| 92 | 6 | FP: 493 |
| 93 | 5 | FP: 493 |
| 94 | 5 | FP: 493 |
| 95 | 5 | EN: 471 |
| 96 | 5 | EP: 473 |
| 97 | 6 | EP: 486 |
| 98 | 6 | EP: 486 |
| 99 | 6 | EP: 473 |
| 100 | 6 | FP: 473 |
| 101 | 6 | EP: 485 |
| 102 | 6 | NMR1: 1.26 (3H, dd, J = 6.3, 23.8 Hz)), 1.99-2.02 (2H, m), 2.77-2.84 (4H, m) 3.54-4.29 (2H, m), 4.42-5.22 (3H, m), 6.93 (1H, s), 7.05 (1H, s), 7.27 (2H, d, J = 8.1 Hz), 7.46 (1H, dd, J = 4.6, 7.6 Hz); EP: 485 |
| 103 | 6 | NMR1: 1.27 (3H, dd, J = 6.1, 23.8 Hz), 1.89-2.12 (2H, m), 2.70-2.94 (4H, m), 3.43-4.11 (2H, m), 4.37-5.15 (3H, m), 6.99 (1H, s), 7.12 (1H, s), 7.18 (2H, d, J = 7.5 Hz), 7.36 (1H, s), 7.89 (2H, d, J = 8.2 Hz), 7.94-7.96 (1H, m), 8.60 (1H, s), 8.68 (1H, d, J = 2.1 Hz), 12.96 (1H, brs); EP: 485 |
| 104 | 6 | EP: 485 |
| 105 | 1, 6 | FP: 523 |
| 106 | 1, 6 | FP: 535 |

TABLE 24

| Ex | Syn | Dat |
|---|---|---|
| 107 | 6 | EP: 513 |
| 108 | 6 | EP: 513 |
| 109 | 6 | EP: 506 |
| 110 | 6 | EP: 512 |
| 111 | 6 | EP: 507 |
| 112 | 6 | FP: 507 |
| 113 | 1, 6 | NMR1: 1.29 (3H, dd, J = 6.3, 23.9 Hz)), 1.98-2.04 (2H, m), 2.20 (3H, s), 2.80-2.85 (4H, m), 3.56-4.15 (2H, m), 4.44-5.22 (3H, m), 7.00 (1H, s), 7.04-7.23 (3H, m), 7.51 (1H, s), 7.85-7.89 (1H, m), 13.28 (1H, brs); FP: 523 |
| 114 | 1, 6 | FP: 523 |
| 115 | 1, 6 | EP: 493 |
| 116 | 1, 6 | EP: 493 |
| 117 | 6 | NMR1: 0.90 (3H, d, J = 6.6 Hz), 1.69-1.88 (1H, m), 2.09 (3H, s), 2.18 (3H, s), 2.40-2.60 (2H, m), 3.53-3.67 (1H, m), 3.70-3.83 (1H, m), 4.35 (1H, dd, J = 5.0, 47.5 Hz), 6.90 (2H, d, J = 10.0 Hz), 7.30 (2H, d, J = 8.3 Hz), 7.46-7.51 (1H, m), 7.65 (1H, d, J = 8.0 Hz), 7.87-7.94 (3H, m), 8.52 (1H, d, J = 4.3 Hz); EP: 487 |
| 118 | 6 | EP: 487 |
| 119 | 6 | FP: 489 |
| 120 | 6 | EP: 499 |
| 121 | 6 | EP: 499 |

INDUSTRIAL APPLICABILITY

The compound of the formula (I) or a salt thereof has a potent EP1 receptor antagonistic action, and can be used as an agent for preventing and/or treating a lower urinary tract symptom or the like.

Sequence Listing Free Text

Under the number title <223> in the following sequence listing, provided is description on "Artificial Sequence". Specifically, the amino acid sequence as set forth as SEQ ID NO: 1 in the sequence listing is an artificially synthesized signal peptide sequence. Furthermore, the amino acid sequence as set forth as SEQ ID NO: 2 in the sequence listing is an artificially synthesized FLAG sequence.

The invention claimed is:

1. A compound of the formula (I) or a salt thereof:

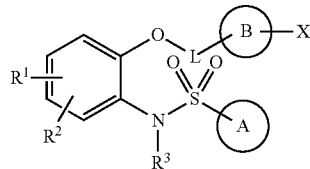

wherein
R¹ and R² are combined with the two adjacent carbon atoms to which they each bind to form a cyclopentene ring;
R³ is 2-fluoropropyl, 2-fluorobutyl, 2,2-difluoroethyl, or 3-fluoro-2-methylpropyl;
L is lower alkylene;
A is pyridyl which may be substituted and B is phenylene which may be substituted or pyridinediyl which may be substituted, or
A is phenyl which may be substituted or pyridyl which may be substituted and B is pyridinediyl which may be substituted;
X is —CO₂R⁰, —CO₂H, or —CO—NH—SO₂—R⁰; and R⁰ is lower alkyl.

2. The compound or a salt thereof according to claim 1, wherein L is methylene.

3. The compound or a salt thereof according to claim 2, wherein A is phenyl substituted with halogen(s), 2-pyridyl, or 3-pyridyl.

4. The compound or a salt thereof according to claim 3, wherein X is —CO₂H or —CO—NH—SO₂—R⁰.

5. The compound or a salt thereof according to claim 4, wherein R³ is 2-fluoropropyl, 2-fluorobutyl, or 3-fluoro-2-methylpropyl.

6. The compound or a salt thereof according to claim 5, wherein B is pyridinediyl, or phenylene which may be substituted with one group selected from the group consisting of methyl, F, and methoxy.

7. The compound or a salt thereof according to claim 1, which is selected from the group consisting of:

4-{[(6-{[(2R)-2-fluoropropyl](pyridin-2-ylsulfonyl)amino}-2,3-dihydro-1H-inden-5-yl)oxy]methyl}benzoic acid, 4-{[(6-{[(2R)-2-fluorobutyl](pyridin-2-ylsulfonyl)amino}-2,3-dihydro-1H-inden-5-yl)oxy]methyl}benzoic acid, 4-{[(6-{[(2S)-2-fluorobutyl](pyridin-2-ylsulfonyl)amino}-2,3-dihydro-1H-inden-5-yl)oxy]methyl}benzoic acid, 4-{[(6-{[(2S)-2-fluoropropyl](pyridin-3-ylsulfonyl)amino}-2,3-dihydro-1H-inden-5-yl)oxy]methyl}benzoic acid, and 4-{[(6-{[(2R)-2-fluoropropyl](pyridin-3-ylsulfonyl)amino}-2,3-dihydro-1H-inden-5-yl)oxy]methyl}benzoic acid, or a salt thereof.

8. A pharmaceutical composition comprising the compound or a salt thereof according to claim 1, and an excipient.

9. A method for treating pollakiuria, comprising administering to a patient in need thereof a therapeutically effective amount of the compound or a salt thereof according to claim 1.

10. The method of claim 9, wherein the pollakiuria is caused by overactive bladder.

11. The compound or a salt thereof according to claim 1, which is 4-{[(6-{[(2R)-2-fluoropropyl](pyridin-2-ylsulfonyl)amino}-2,3-dihydro-1H-inden-5-yl)oxy]methyl}benzoic acid or a salt thereof.

12. The compound or a salt thereof according to claim 1, which is 4-{[(6-{[(2R)-2-fluorobutyl](pyridin-2-ylsulfonyl)amino}-2,3-dihydro-1H-inden-5-yl)oxy]methyl}benzoic acid or a salt thereof.

13. The compound or a salt thereof according to claim 1, which is 4-{[(6-{[(2S)-2-fluorobutyl](pyridin-2-ylsulfonyl)amino}-2,3-dihydro-1H-inden-5-yl)oxy]methyl}benzoic acid or a salt thereof.

14. The compound or a salt thereof according to claim 1, which is 4-{[(6-{[(2S)-2-fluoropropyl](pyridin-3-ylsulfonyl)amino}-2,3-dihydro-1H-inden-5-yl)oxy]methyl}benzoic acid or a salt thereof.

15. The compound or a salt thereof according to claim 1, which is 4-{[(6-{[(2R)-2-fluoropropyl](pyridin-3-ylsulfonyl)amino}-2,3-dihydro-1H-inden-5-yl)oxy]methyl}benzoic acid or a salt thereof.

* * * * *

SEQUENCE LISTING

<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Lys Thr Ile Ile Ala Leu Ser Tyr Ile Phe Cys Leu Val Phe Ala
1               5                   10                  15

<210> SEQ ID NO 2

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Tyr Lys Asp Asp Asp Asp Lys
1               5
```